US012678053B2

(12) United States Patent
Molly Subhash et al.

(10) Patent No.: US 12,678,053 B2
(45) Date of Patent: Jul. 14, 2026

(54) TECHNOLOGIES FOR THREE-DIMENSIONAL SPECTROSCOPIC IMAGING OF TISSUE PROPERTIES

(71) Applicant: Colgate-Palmolive Company, New York, NY (US)

(72) Inventors: Hrebesh Molly Subhash, Somerset, NJ (US); Benny E. Urban, Jr., Somerset, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 98 days.

(21) Appl. No.: 18/579,071

(22) PCT Filed: Jul. 1, 2022

(86) PCT No.: PCT/US2022/035982
§ 371 (c)(1),
(2) Date: Jan. 12, 2024

(87) PCT Pub. No.: WO2023/287599
PCT Pub. Date: Jan. 19, 2023

(65) Prior Publication Data
US 2024/0324884 A1      Oct. 3, 2024

Related U.S. Application Data

(60) Provisional application No. 63/221,634, filed on Jul. 14, 2021.

(51) Int. Cl.
A61B 5/00 (2006.01)

(52) U.S. Cl.
CPC .......... A61B 5/0088 (2013.01); A61B 5/0035 (2013.01); A61B 5/0071 (2013.01);
(Continued)

(58) Field of Classification Search
CPC ... A61B 5/0088; A61B 5/0035; A61B 5/0071; A61B 5/0073; A61B 5/441; A61B 5/442;
(Continued)

(56) References Cited

U.S. PATENT DOCUMENTS 6,640,130 B1    10/2003    Freeman et al.
7,945,077 B2    5/2011    Demos
(Continued)

FOREIGN PATENT DOCUMENTS

WO        2020/124151        6/2020
WO        2020/146489        7/2020

OTHER PUBLICATIONS

Sibai, Mira, et al. "Preclinical evaluation of spatial frequency domain-enabled wide-field quantitative imaging for enhanced glioma resection." Journal of biomedical optics 22.7 (2017): 076007-076007. (Year: 2017).*
(Continued)

*Primary Examiner* — Sean D Mattson

(57) ABSTRACT

Technologies are disclosed for an imaging device that may indicate at least one property of a tissue sample. The device may project light on the tissue sample. The device may control a capture of hyperspectral fluorescence image data of the tissue sample. The device may control a capture of spatial frequency domain imaging (SFDI) image data of the tissue sample. The device may process a first computational overlap of the hyperspectral fluorescence image data and the SFDI image data. The device may determine one or more properties of the first location of the tissue sample based on the first computational overlap of the hyperspectral fluorescence image data and the SFDI image data. The device may generate a 2D or a 3D spatial visual representation of the
(Continued)

first location of the tissue sample based on the first computational overlap of the hyperspectral fluorescence image data and the SFDI image data.

20 Claims, 16 Drawing Sheets

(52) U.S. Cl.
CPC ............ *A61B 5/0073* (2013.01); *A61B 5/441*
(2013.01); *A61B 5/442* (2013.01); *A61B 5/443*
(2013.01); *A61B 5/445* (2013.01); *A61B*
*5/4542* (2013.01); *A61B 5/4547* (2013.01);
*A61B 5/4552* (2013.01)

(58) Field of Classification Search
CPC ....... A61B 5/443; A61B 5/445; A61B 5/4542;
A61B 5/4547; A61B 5/4552; A61B
5/14551; A61B 5/444
See application file for complete search history.

(56) References Cited

U.S. PATENT DOCUMENTS

| | | | |
|---|---|---|---|
| 8,320,996 | B2 | 11/2012 | Panasyuk et al. |
| 8,406,859 | B2 | 3/2013 | Zuzak et al. |
| 8,761,476 | B2 | 6/2014 | Burlina et al. |
| 9,078,619 | B2 | 7/2015 | Panasyuk et al. |
| 9,619,883 | B2 | 4/2017 | Yudovsky |
| 9,766,382 | B2 | 9/2017 | Darty |
| 10,066,997 | B2 | 9/2018 | Korner et al. |
| 10,130,260 | B2 | 11/2018 | Patwardhan |
| 10,307,098 | B2 | 6/2019 | Gareau |
| 10,438,356 | B2 | 10/2019 | Dacosta |
| 10,666,928 | B2 | 5/2020 | Liu |
| 10,768,114 | B2 | 9/2020 | Franjic et al. |
| 10,849,710 | B2 | 12/2020 | Liu |
| 10,964,018 | B2 | 3/2021 | Marrero Callico et al. |
| 11,304,699 | B2 | 4/2022 | Shelton, IV et al. |
| 2002/0173723 | A1 | 11/2002 | Lewis et al. |
| 2007/0224694 | A1 | 9/2007 | Puchalski |
| 2009/0118622 | A1* | 5/2009 | Durkin ............... G01N 21/6456 |
| | | | 600/473 |
| 2014/0321728 | A1 | 10/2014 | Chin |
| 2016/0278678 | A1* | 9/2016 | Valdes ............... A61B 5/14546 |
| 2017/0135646 | A1 | 5/2017 | Chin |
| 2018/0042483 | A1 | 2/2018 | Bardhan et al. |
| 2018/0270474 | A1* | 9/2018 | Liu ...................... A61B 5/0064 |
| 2019/0113423 | A1 | 4/2019 | Goodman et al. |
| 2019/0117078 | A1* | 4/2019 | Sharma .................... A61B 1/24 |
| 2019/0269363 | A1* | 9/2019 | Vilenskii ................ A61B 5/444 |
| 2020/0375521 | A1 | 12/2020 | Hadoux et al. |
| 2021/0186610 | A1 | 6/2021 | Zuo et al. |
| 2021/0239617 | A1* | 8/2021 | Paulsen ................ A61B 5/4887 |
| 2024/0304337 | A1* | 9/2024 | Wang .................... G16H 50/50 |

OTHER PUBLICATIONS

Applegate, Matthew B., Samuel S. Spink, and Darren Roblyer. "Dual-DMD hyperspectral spatial frequency domain imaging (SFDI) using dispersed broadband illumination with a demonstration of blood stain spectral monitoring." Biomedical Optics Express 12.1 (2020): 676-688. (Year: 2020).*

Sibai, Mira, et al. "Quantitative fluorescence imaging enabled by spatial frequency domain optical-property mapping in the sub-diffusive regime for surgical guidance." Molecular-Guided Surgery: Molecules, Devices, and Applications. vol. 9311. SPIE, 2015. (Year: 2015).*

International Search Report and Written Opinion issued in PCT International Application No. PCT/US2022/035982, mailed Oct. 11, 2022, pp. 1-8.

Sibai, Mira et al.: "Quantitative fluorescence imaging enabled by spatial frequency domain optical-property mapping in the sub-diffusive regime for surgical guidance," Progress in Biomedical Optics and Imaging, Spie-International Society for Optical Engineering, Bellingham, WA, US, vol. 9311, Mar. 4, 2015 (Mar. 4, 2015), pp. 1-15.

Urban, et al., "Multimodal hyperspectral fluorescence and spatial frequency domain imaging for tissue health diagnostics of the oral cavity," Optical Society of America, Biomedical Optics Express, vol. 12, No. 11, Nov. 1, 2021, pp. 1-15.

* cited by examiner

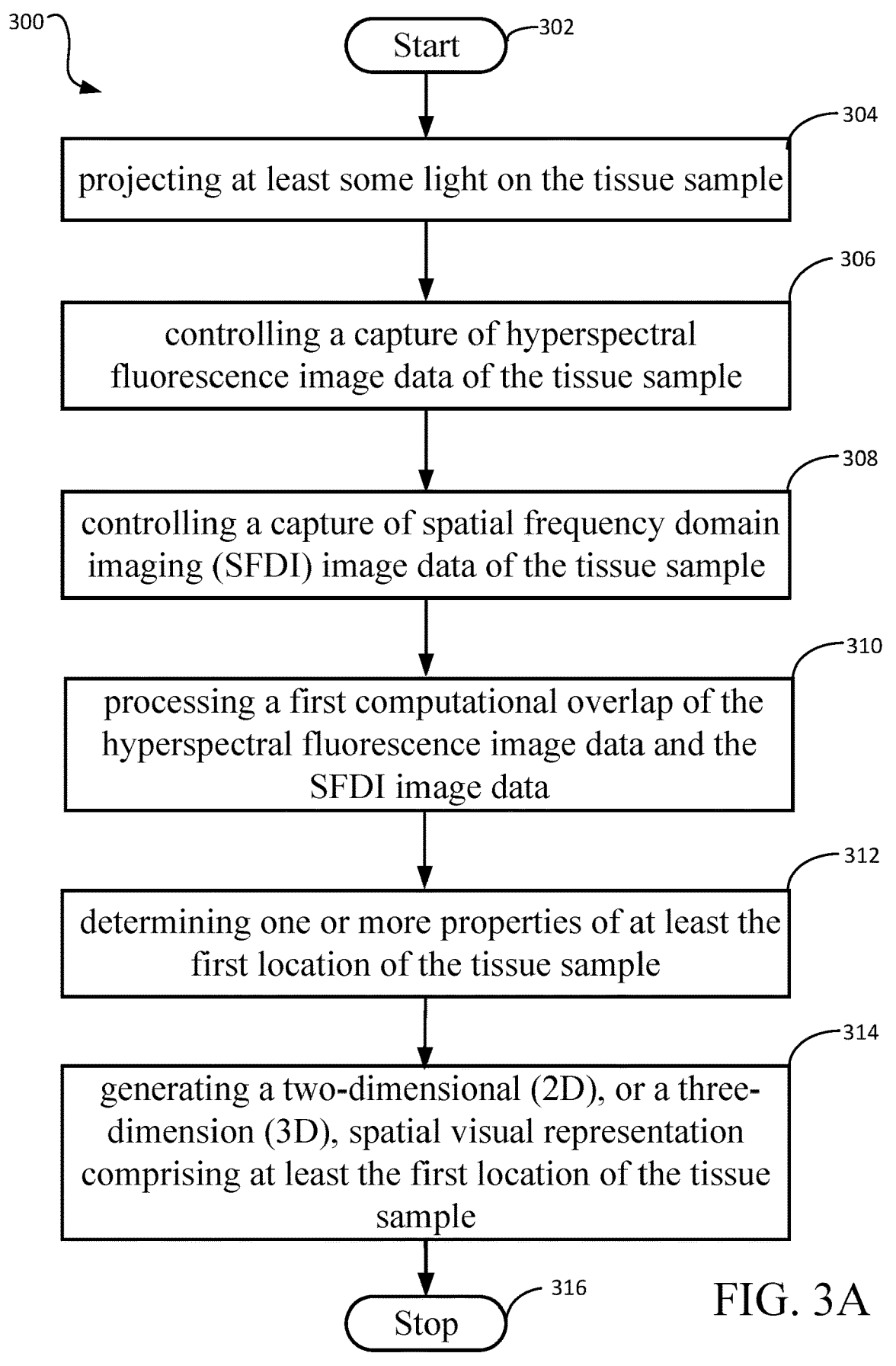

300

302 — ( Start )

304 projecting at least some light on the tissue sample

306 controlling a capture of hyperspectral fluorescence image data of the tissue sample

308 controlling a capture of spatial frequency domain imaging (SFDI) image data of the tissue sample

310 processing a first computational overlap of the hyperspectral fluorescence image data and the SFDI image data

312 determining one or more properties of at least the first location of the tissue sample

314 generating a two-dimensional (2D), or a three-dimension (3D), spatial visual representation comprising at least the first location of the tissue sample 316 — ( Stop )

FIG. 3A

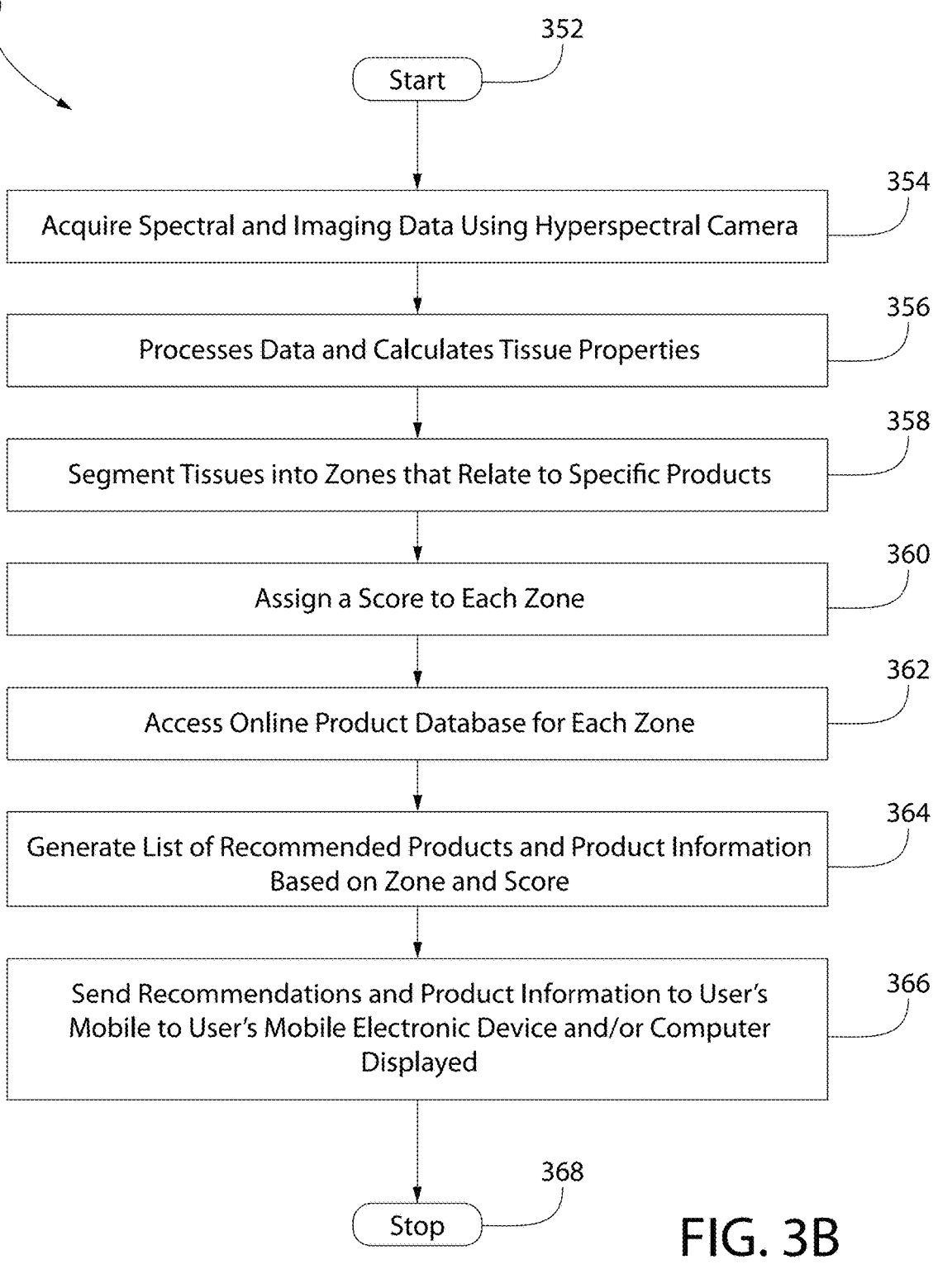

350

352

Start

354

Acquire Spectral and Imaging Data Using Hyperspectral Camera

356

Processes Data and Calculates Tissue Properties

358

Segment Tissues into Zones that Relate to Specific Products

360

Assign a Score to Each Zone

362

Access Online Product Database for Each Zone

364

Generate List of Recommended Products and Product Information Based on Zone and Score

366

Send Recommendations and Product Information to User's Mobile to User's Mobile Electronic Device and/or Computer Displayed

368

Stop

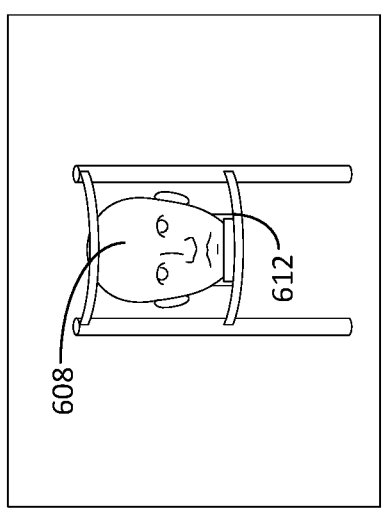
FIG. 6C
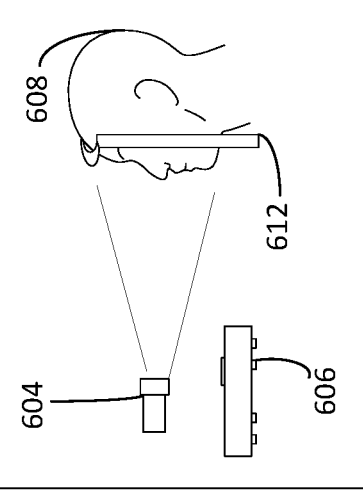
FIG. 6B
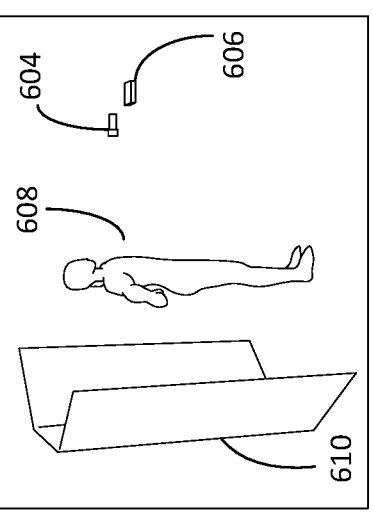
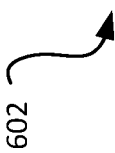
FIG. 6A

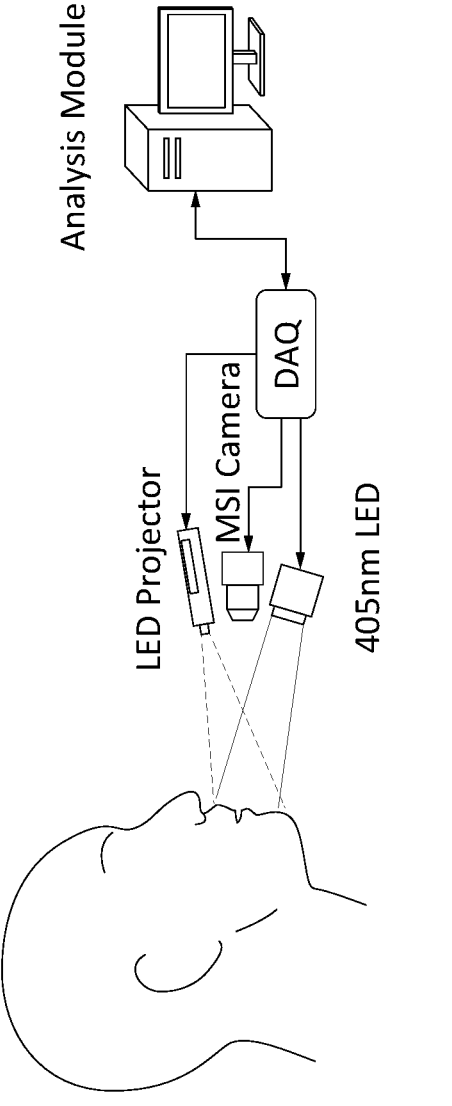
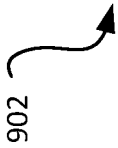
FIG. 9

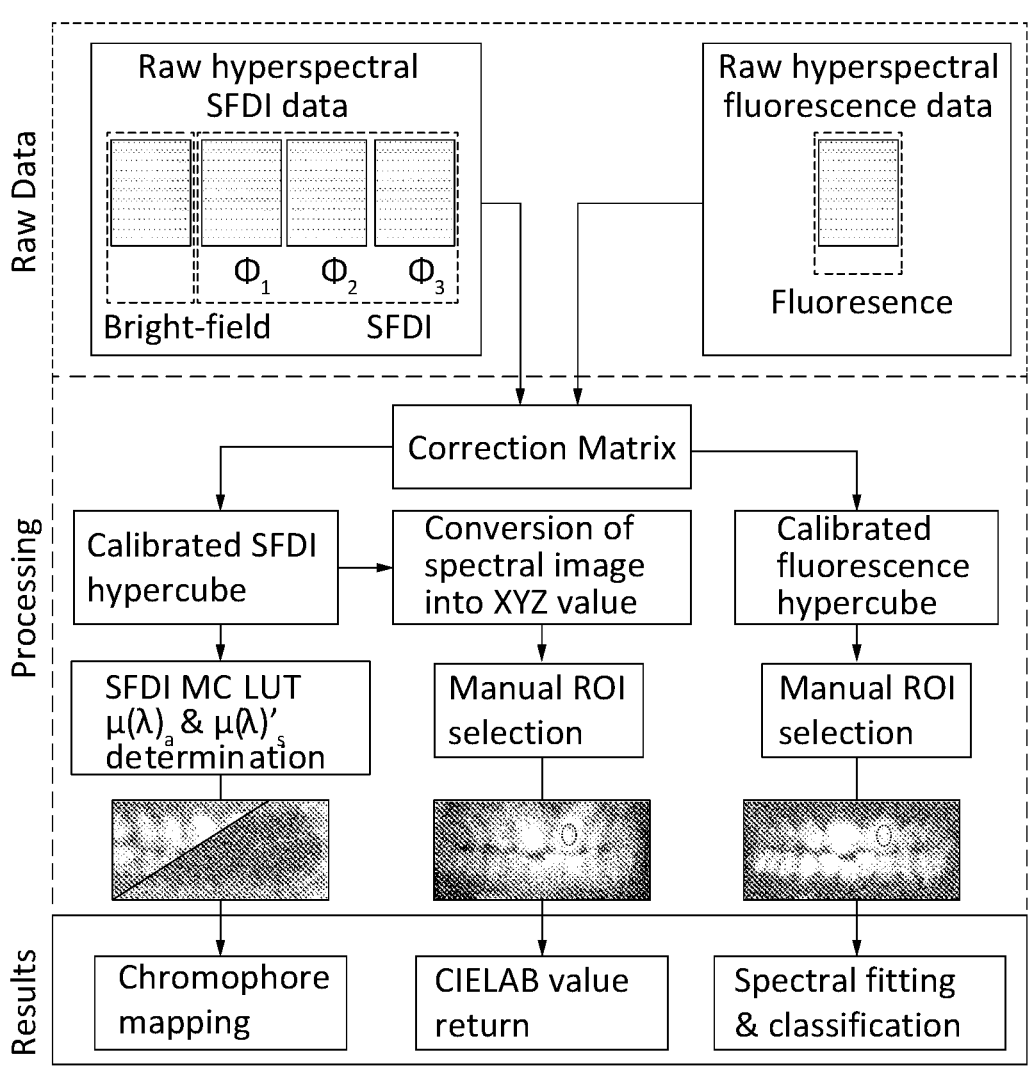
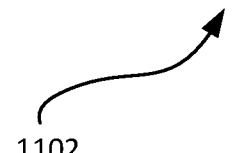
FIG. 11

Fluoresence
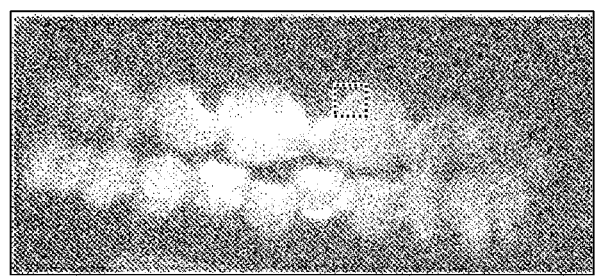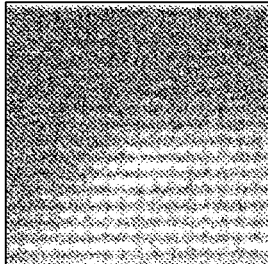
Bright-field
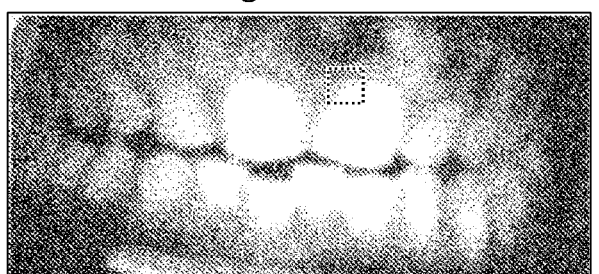
FIG. 12A
Hypercube
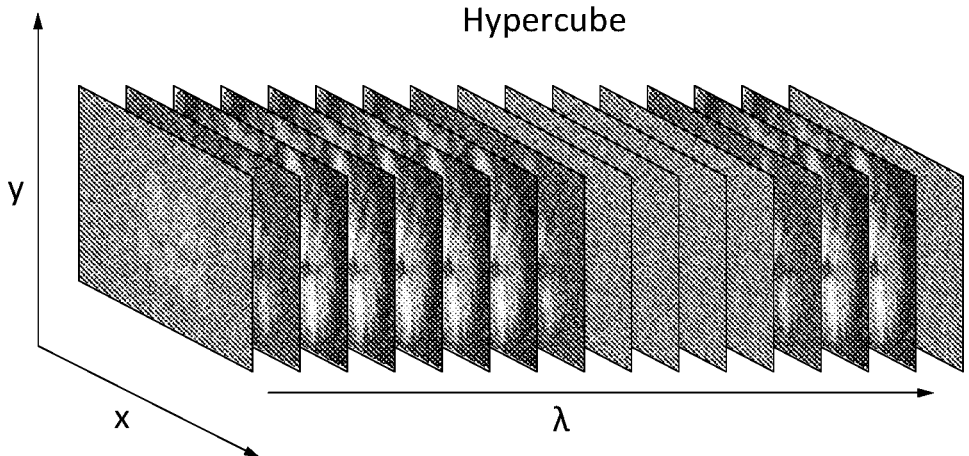
FIG. 12B

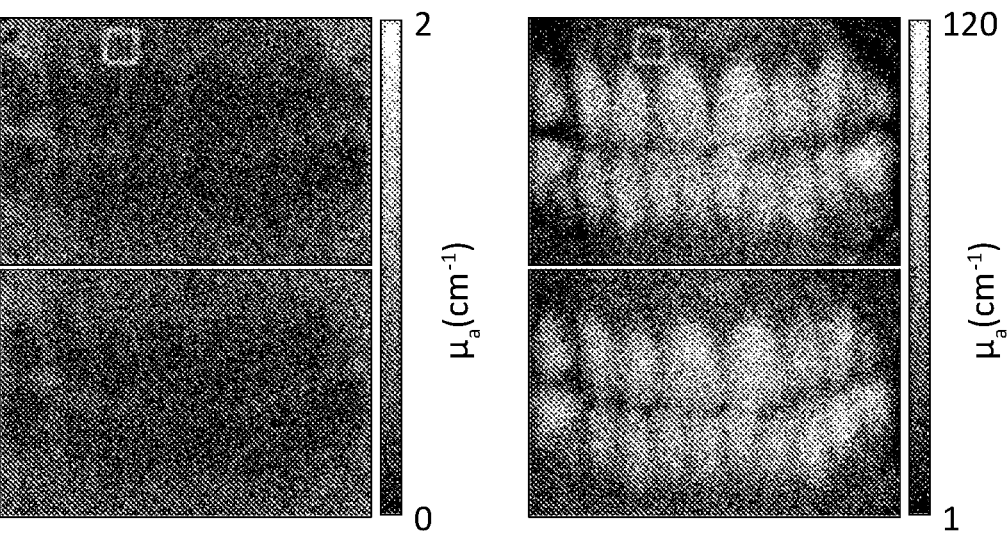
FIG. 13A                    FIG. 13B
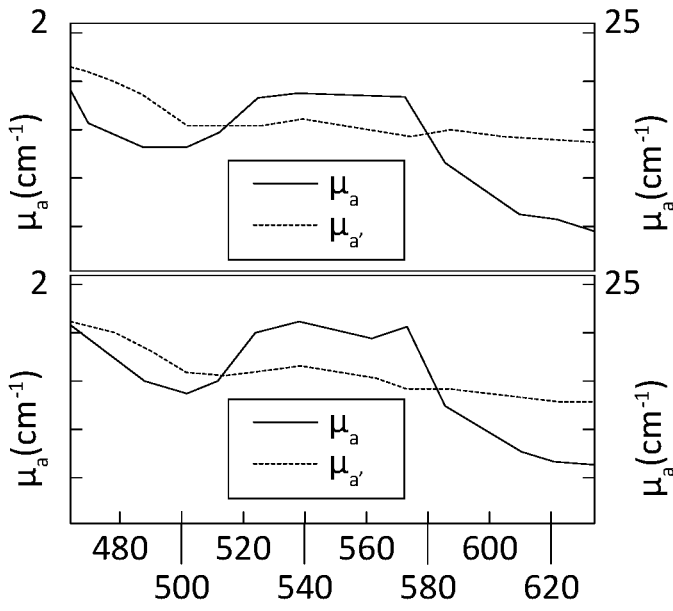
FIG. 13C

CIE - L*a*b* coordinates

TECHNOLOGIES FOR THREE-DIMENSIONAL SPECTROSCOPIC IMAGING OF TISSUE PROPERTIES

CROSS-REFERENCE TO RELATED APPLICATIONS

This application claims the benefit of U.S. Provisional Patent Application No. 63/221,634, filed on Jul. 14, 2021, the entire contents of which being hereby incorporated by reference herein, for all purposes.

BACKGROUND

Dental tissue issues such as, for example, periodontal disease and tooth cavities are often caused by certain bacterial species in the mouth that interact with proteins present in saliva to form a film, known as plaque, that coats the teeth. If this biofilm build up progresses, the acid produced by the bacteria can attack the teeth resulting in tooth decay. The plaque also may attack the soft gum tissue of the mouth leading to gingivitis, which affects the gums, or periodontitis, which may affect all of the soft tissue and bone supporting the teeth.

Dehydrated skin is another undesirable tissue condition that, when left untreated, can cause itching, cracking and bleeding of skin due to lack of elasticity. Cracked and bleeding skin can potentially lead to infection and inflammation of tissue. In some cases, dry skin is an indicator of atopic dermatitis, which can trigger eczema. In the long term, dry skin can lead to permanent cracking and unaesthetic appearance, along with other health problems.

SUMMARY

Technologies are disclosed for an imaging device that may be configured to indicate at least one property of a tissue sample. The imaging device may comprise a memory and/or a light emitting projector. The imaging device may comprise a camera and/or a processor. The processor may be configured to project at least some light on the tissue sample. The processor may be configured to control a capture of hyperspectral fluorescence image data of the tissue sample, the hyperspectral fluorescence image data corresponding at least to a first location in the tissue sample.

The processor may be configured to control a capture of spatial frequency domain imaging (SFDI) image data of the tissue sample. The SFDI image data may correspond at least to the first location in the tissue sample. The processor may be configured to process a first computational overlap of the hyperspectral fluorescence image data and the SFDI image data. The first computational overlap may comprise at least the first location in the tissue sample.

The processor may be configured to determine one or more properties of at least the first location of the tissue sample based, at least in part, on the first computational overlap of the hyperspectral fluorescence image data and the SFDI image data. The processor may be configured to generate a two-dimensional (2D), or a three-dimension (3D), spatial visual representation comprising at least the first location of the tissue sample based, at least in part, on the first computational overlap of the hyperspectral fluorescence image data and the SFDI image data.

Technologies are disclosed for one or more techniques/methods for indicating at least one property of a tissue sample. One or more techniques may be performed by an imaging device, where the imaging device may comprise a memory, a light emitting projector, a camera, and/or a processor. One or more techniques may comprise projecting at least some light on the tissue sample.

One or more techniques may comprise controlling a capture of hyperspectral fluorescence image data of the tissue sample. The hyperspectral fluorescence image data may correspond at least to a first location in the tissue sample. One or more techniques may comprise controlling a capture of spatial frequency domain imaging (SFDI) image data of the tissue sample. The SFDI image data may correspond at least to the first location in the tissue sample.

One or more techniques may comprise processing a first computational overlap of the hyperspectral fluorescence image data and the SFDI image data. The first computational overlap may comprise at least the first location in the tissue sample. One or more techniques may comprise determining one or more properties of at least the first location of the tissue sample based, at least in part, on the first computational overlap of the hyperspectral fluorescence image data and the SFDI image data.

One or more techniques may comprise generating a two-dimensional (2D), or a three-dimension (3D), spatial visual representation that may comprise at least the first location of the tissue sample based, at least in part, on the first computational overlap of the hyperspectral fluorescence image data and the SFDI image data.

BRIEF DESCRIPTION OF DRAWINGS

The elements and other features, advantages and disclosures contained herein, and the manner of attaining them, will become apparent and the present disclosure will be better understood by reference to the following description of various examples of the present disclosure taken in conjunction with the accompanying drawings, wherein:

FIG. 3A is a flow diagram of an example technique for indicating at least one property of a tissue sample.

FIG. 3B is a flow diagram of an example technique for indicating at least one property of a tissue sample.

FIG. 6A, FIG. 6B, and FIG. 6C illustrate an example of a large field-of-view (FOV) 3D hyperspectral imaging device and configuration.

FIG. 9 illustrates an example schematic of an example Hy-F-SFDI system/device.

FIG. 11 is an example technique flow of Hy-F-SFDI system/device data processing.

FIG. 12A and FIG. 12B illustrates an example of the raw hyperspectral fluorescence and bright-field images and a hypercube of spectral imaging.

FIG. 13A, FIG. 13B, and FIG. 13C illustrate Hy-F-SFDI analysis results for mapped tissue absorption coefficients at the 502 nm spectral channel over several weeks.

DETAILED DESCRIPTION

Figure 1:
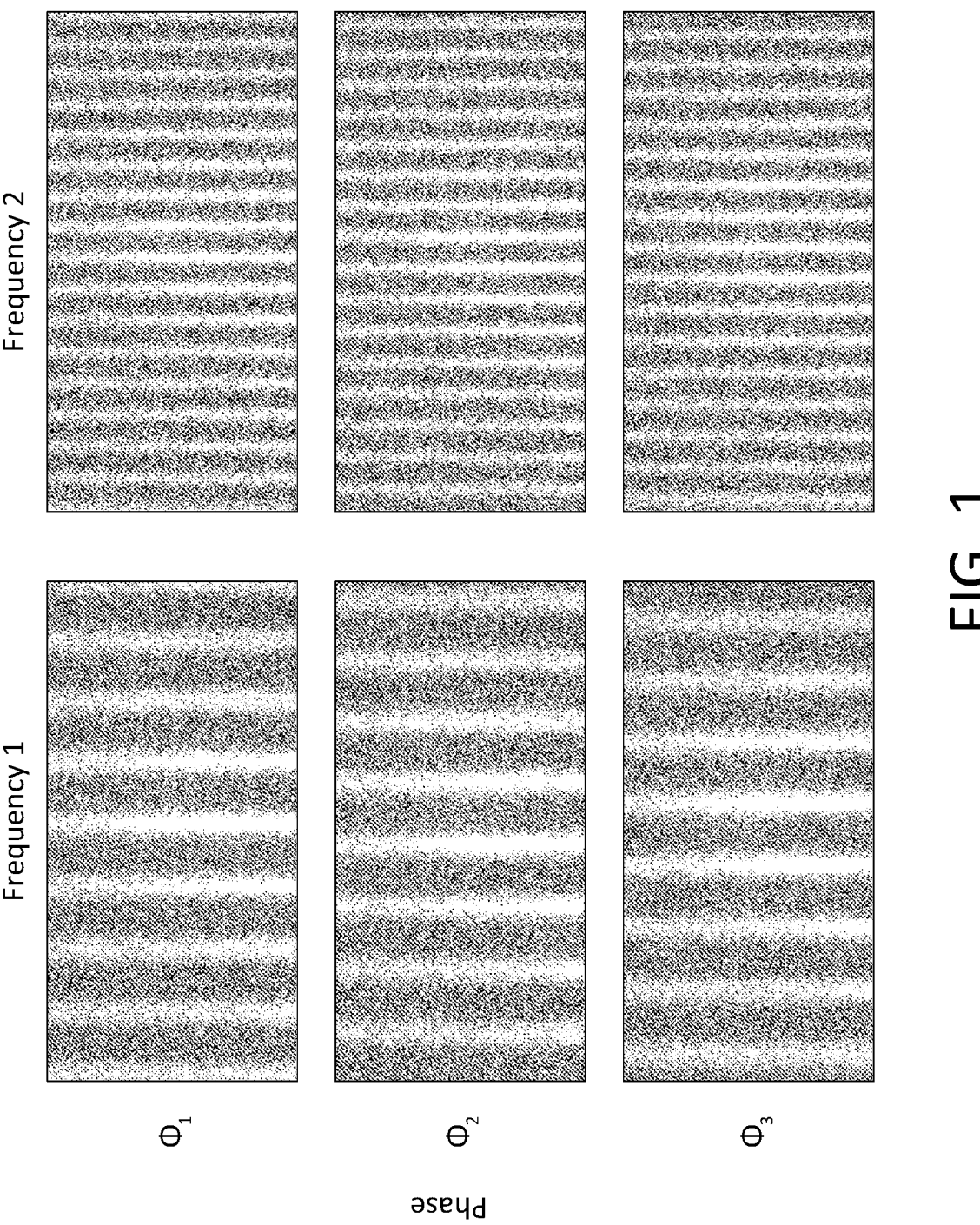
FIG. 1 is an illustration of an example illumination pattern of a sinusoidal grating structure.

For the purposes of promoting an understanding of the principles of the present disclosure, reference will now be made to the examples illustrated in the drawings, and specific language will be used to describe the same. It will nevertheless be understood that no limitation of the scope of this disclosure is thereby intended.

Tissue health problems can take many forms, such as tooth decay, oral cancer, periodontal disease, melanoma, acne, infection, melanoma, and dry skin. There is currently an unmet need for the development of a sensitive and accurate quantitative diagnostic tool that can provide three-dimensional (3D) structural, functional and spectroscopic information for early detection and diagnosis of tissue conditions.

Gingivitis is an inflammation of the gums characterized by redness, swelling, bleeding, and sensitivity. These changes result from an accumulation of biofilm along the gingival margins and the immune system's inflammatory response to the release of destructive bacterial byproducts. Gingivitis results in increased vascularity and morphological change in the vascular architecture, hemodynamics, tissue oxygenation and surrounding tissue color and shape. Monitoring and assessment of local inflammatory hemodynamic profiles such as tissue oxygen saturation (StO2), total tissue hemoglobin (tHb), deoxyhemoglobin (Hb), oxygenated hemoglobin (HbO2) of gingiva, gingiva shape and size during disease progression and response to therapy is crucial for understanding the pathophysiology. The early stages of gingivitis are reversible thorough proper treatment with over-the-counter products. Without adequate oral hygiene, however, chronic infections and periodontitis can develop.

Monitoring and assessing tissue hydration and inflammation is useful in determining tissue health and preventing dehydrated skin. Treating dehydrated skin with over-the-counter skin hydrating products can prevent undesirable skin tissue effects. However, different stages of the dry skin, different areas of the body, and different tissue types benefit more from a variety of specialized products which can improve tissue health.

There are no current reliable clinical imaging systems currently available for monitoring indicators of tissue health such as morphological changes, dynamics of functional information and abundant spectroscopic information in vivo in a timely 3D quantitative manner. There are no automated methods used in combination with such devices/systems that can make specific recommendation based on quantitative diagnostic results.

Optical scanner imaging technology shows promise for a wide range of diagnostic applications with capabilities for high-resolution, 3D modeling of tissue morphology. However, current 3D scanner technology for clinical applications applies traditional red-green-blue (RGB) or monochrome sensors for 3D imaging. RGB sensors might be incapable of measuring the higher-level spectroscopic information necessary for diagnosing many types of tissue conditions. 3D handheld scanner probe technology has recently been adopted for clinical diagnosis of hard and soft tissues in oral and maxillofacial regions. These scanners can employ color sensors and image stitching algorithms to reconstruct large field-of-view images in color.

In one or more scenarios, 3D scanners can be used to longitudinally monitor diseases related to gingiva and cavities in the teeth, where color and morphology are affected. However, current 3D scanner technology can only provide structural and RGB texture information of tissues, and/or may be incapable of providing critical information about physiological parameter, such as oxygen saturation of hemoglobin, oxygen metabolic rate, hydration, collagen density, or sub-surface angiography. Tissue oxygenation, angiography, hydration and collagen density are important parameters in diagnosing abnormal conditions.

Hyperspectral imaging is an imaging modality that has found application in biological diagnostics. Hyperspectral imaging can detect wavelengths that penetrate deeper into tissue, thereby allowing sub-surface tissue imaging. Perhaps because of the high-level spectroscopic data, among other reasons, functional imaging is possible using hyperspectral imaging. Hyperspectral imaging refers to a conglomerate of spectral imaging techniques, such as point scan, line scan, and snapshot hyperspectral imaging, which generally use 1D or 2D array detectors for spectral imaging. Hyperspectral imaging has been widely applied in agriculture for determining crop health, geology for mineral determination, astronomy for atomic composition determination, environmental and chemical science for chemical imaging, and in industrial machine vision for digital sorting. Hyperspectral imaging has also found application in biomedical imaging for eye diagnostics (fundus imaging) and skin health evaluation. However, hyperspectral widefield imaging cannot distinguish absorption/scattering properties of samples and also lacks 3D spatial imaging capabilities.

Spatial frequency domain imaging (SFDI) is a technique for quantitative separation of absorption from scattering in turbid media. SFDI employs the spatial frequency domain for spatial mapping of optical properties. In SFDI, periodic structured light is projected onto a sample as shown in FIG. 1. A 2D array detector (not shown) may be used to capture the back scattered/reflected light. Each pixel of the 2D array functions as a point measurement to determine the optical properties of the corresponding point of the sample. This technique eliminates the need for raster scanning. After digitally recording the light on the detector, optical properties of different tissue layers are mathematically determined using the wavelength dependent diffusion approximation with the Boltzmann transport equation. This enables SFDI to map melanin concentration and monitor hemodynamics in vivo, and further allows sub-surface imaging into tissue.

SFDI devices/systems may use broadband illumination sources in combination with tunable filters and/or tunable illumination sources with monochromatic detectors to determine tissue optical properties. However, these methods increase image acquisition time and limit the application for clinical application, where snapshot imaging is essential. Additionally, by applying a triangulation algorithm/computational overlap algorithm, 3D image reconstruction is possible using the same frequency patterns from SFDI.

Systems, devices, and/or techniques that may overcome the aforementioned limitations and/or issues may be useful.

Described herein, devices/systems/techniques may combine snapshot hyperspectral imaging with SFDI and triangulation/computational overlap, perhaps for example to allow 3D non-invasive in vivo spectral imaging of tissues. One or more techniques described herein can be used for tissue health diagnostics, longitudinal disease monitoring, product/drug efficacy investigations and/or product recommendations.

The subject matter herein describes tissue imaging and/or diagnostic systems/devices/techniques and/or methods/techniques/deices for automated product selection. For example, some devices/techniques described herein pertain to imaging tissue morphological, chromographical, and functional information for the diagnosis and/or monitoring of tissue conditions. One or more devices/techniques may evaluate tissue condition and returns a score for different tissue zone and recommends care products to the user based on scoring and zone location. One or more devices/techniques may feed diagnostic information to a cloud database of consumer products. The database may contain information about the best consumer product for the diagnosed individual/condition. The database may provide the diagnosed individual information about the recommended product, such as ingredients, usage frequency, and/or dosage. The diagnostic data, product recommendations and information may be directly sent to the diagnosed individual's mobile device or read directly from a computer display. Other/alternate product suggestions can be made from user input and feedback, such as allergies and/or product discomfort.

Described herein are one or more devices/methods/techniques for simultaneous spectroscopic imaging of multi-dimensional structures, quantifying chronographic and functional information (including vascular hemodynamics, tissue oxygen concentration) and method for automated product selection based on tissue zone scoring. The devices/technique may use the combined principles of spatial-frequency domain imaging, hyperspectral imaging, and position triangulation/computational overlap to determine tissue properties. The device/techniques may utilize one or more hyperspectral cameras with integrated multi-wavelength laser diode (LD), and/or LED arrays and/or broadband illumination sources that are either continuous or pulsed, and an integrated light shaping/pattering/modulating device, such as a digital micromirror device (DMD) array, digital light processing (DLP) array, grating, projector, optic, or mask, to pattern the integrated light source.

The data generated from the devices/techniques may be used by a computer vision algorithm to segment the tissue into different zones. The devices/techniques may use a machine learning algorithm to assign each zone a score based on the tissue properties. The zone and/or score may be used to select best products from a product database. The selection process may be automated. Perhaps for example after product selection, among other scenarios, tissue parameters, product recommendation, product information, and product usage information are displayed to the user via computer screen or user mobile device. One or more devices/techniques may permit routine measurements to be made of tissue morphology, tissue anatomy, tissue hydration, tissue collagen, tissue function, tissue oxy-deoxygenation, and total hemoglobin, allowing for more informed product decisions and application. As a diagnostic tools, one or more devices/techniques can also aid in longitudinal monitoring of tissue conditions.

One or more devices/techniques described herein may provide quantitative tissue diagnostics and/or product recommendations. For example, the devices/techniques may diagnose tissue conditions.

The device composes a snapshot hyperspectral camera for simultaneous image acquisition and 2D spectroscopic mapping. The image and spectroscopic information may be transferred to a computer via cable or wireless signal. The device may include a broadband or monochromatic patterned illumination source for illuminating tissue. The illumination source may be singular or an array of lasers, LEDs, LDs, SLEDs, arc or incandescent lights. The illumination wavelength may range from ultraviolet to far-infrared, including short wavelength infrared. The illumination source may be continuous or pulsed. The illumination source may be patterned using a DMD array, DLP array, grating, projector, optic, or mask. The incident patterned light may be patterned as gratings, mesh, straight lines, diagonal lines, curved lines, bars, checkers, or circular structures. Examples of an illumination pattern may be a sinusoidal grating structure, as shown in FIG. 1.

In one or more scenarios, perhaps for example for sinusoidal grating structure illumination, the illumination intensity may be modeled by: $I(x,y,z)=I_o(z)\cos(\omega_x x+\Phi_x)\cos(\omega_y y+\Phi_y)$, where I is measured intensity, $I_o$ is intensity at the sample, $\omega$ is the modulation frequency, $\omega=2\pi f$, and $\Phi$ is the phase. For the case where illumination intensity is modulated in only the x-dimension, the equation simplifies to: $I=I_o(z)\cos(\omega_x x+\Phi_x)$. The light may be phase shifted multiple times to cover all of k-space. In examples, the phase may be shifted in steps of $$\Delta\Phi = \frac{2\pi}{3}.$$

Polarizers or similar optics may be placed in front of the illumination source and the hyperspectral camera to reject specular reflectance, which may lead to measurement error. Other optics may be placed in front of the illumination source to collimate, focus, de-focus, magnify or de-magnify the illumination. A new image may be acquired during each phase shift of the illumination pattern. In some examples, the frequency of the pattern may be changed and/or phase shifted multiple times to better approximate the optical absorbance, reflectance, and/or transport length of the tissue.

Figures 2A, 2B, 2C:
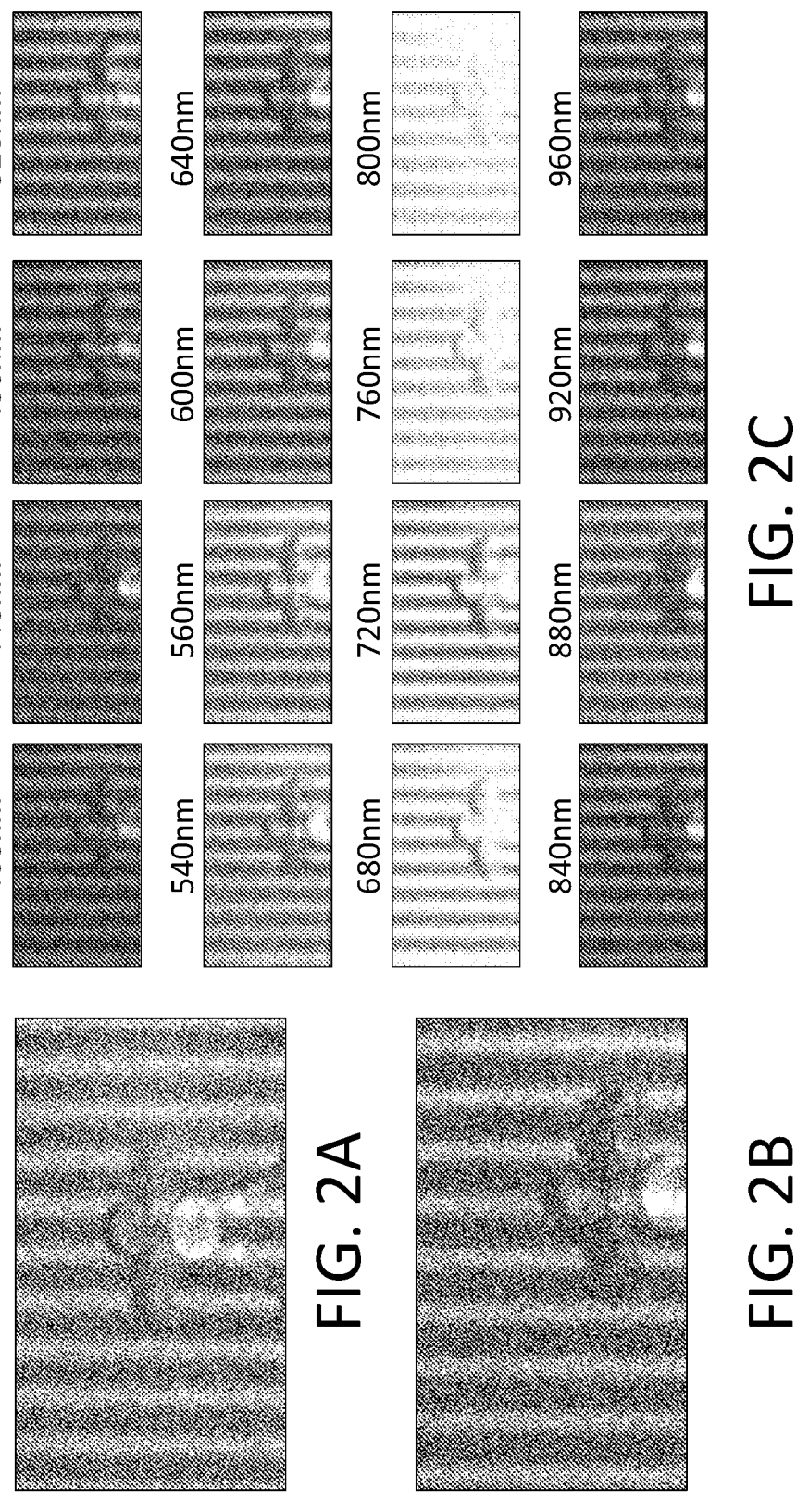
FIG. 2A, FIG. 2B, and FIG. 2C illustrate example images of raw hyperspectral image, an RGB image, and spectral channels.

After acquisition of one or more (e.g., all) hyperspectral images from the different phase and frequency patterns, the data may be transferred to a computer for processing. For processing, the hyperspectral image may be acquired (e.g., first acquired) in a hyperspectral data cube and then segmented where images (e.g., all images) may be separated by their respective wavelength channel, as shown in FIG. 2A, FIG. 2B, and FIG. 2C. FIG. 2A illustrates an example of a raw hyperspectral image. FIG. 2B illustrates an example of a black and white representation of a RGB image. FIG. 2C illustrates an example of spectral channels. To improve measurements, the optical background may be subtracted from all images. The DC intensity image, $I_{DC}$, may be recovered by summing the three phases of images acquired at a single frequency:

$$I_{DC} = \frac{1}{3}[I_1 + I_2 + I_3].$$

Figure 5:
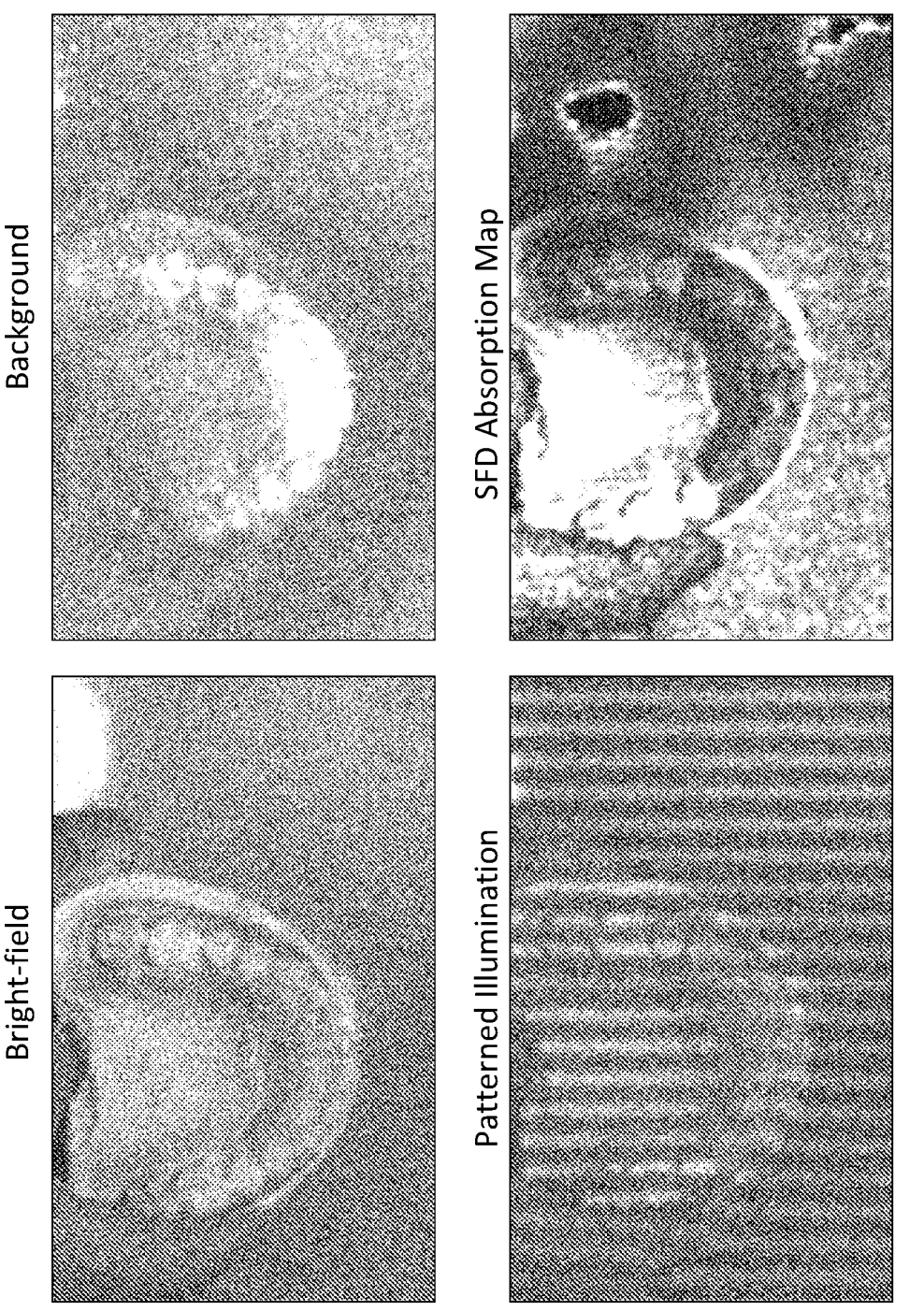
FIG. 5 illustrates an example of bright-field imaging, background imaging, pattern illuminated imaging, and SFD absorption map imaging.

The AC intensity components may be recovered using the equation: $I_{AC} = \sqrt{(I_1-I_2)^2+(I_2-I_3)^2+(I_3-I_1)^2}$. In processing, the phase shift along the non-modulated dimension due to the non-planar surface may also be used for volumetric determination by using the principles of triangulation/computational overlap. This process may be repeated for every wavelength available in the hyperspectral data cube. The measured modulation intensity for each wavelength may be used to determine the effective scattering coefficient, $\mu'_s$, absorption coefficient, $\mu_a$, and optical correlation length, $l_c$, of the tissue is derived using the principles of spatial frequency domain (SFD) imaging. An example is shown in FIG. 5, with bright-field imaging, background imaging, pattern illuminated imaging, and an SFD absorption map imaging.

The absorption and scattering at each measured wavelength may then be used to quantitatively map the tissue properties in three-dimensions using, for example a computer algorithm. These wavelengths may include oxy-deoxy hemoglobin absorption peeks, isosbestic points, water, lipid and collagen absorptions peaks at visible, near infrared, short-wave-infrared ranges, far-infrared and/or millimeter wavelengths.

FIG. 6A shows an example of a large FOV 3D snapshot hyperspectral imaging device based on SFDI and position triangulation/computational overlap, for example. The device/system may have one or more hyperspectral cameras 604 and one or more structured illuminators 606 for illuminating a sample 608. In one or more scenarios, mirrors 610 may be located around the sample 608 to get a snapshot 3D hyperspectral image (not shown). The camera 604 may be connected to a computer (not shown) via wire or wireless connection. The computer may calculate the absorption/reflection properties of the tissue sample at one or more, or each, spectral wavelength available from the camera 604 and/or may map the optical properties to its 3D spatial location using mathematical triangulation/computational overlap. When employing mirrors 610 for 360 degree imaging, a snapshot (e.g., only a single snapshot) may be useful/needed at one or more, or each, phase and/or frequency. In one or more scenarios, stitching may be useful/necessary if scanning, for example. FIG. 6B shows another example of the device for face tissue data acquisition. In FIG. 6B a chin rest 612 may be used to stabilize the patient/sample 608 to reduce image artifacts, as shown via from view in FIG. 6C.

Figure 7B:
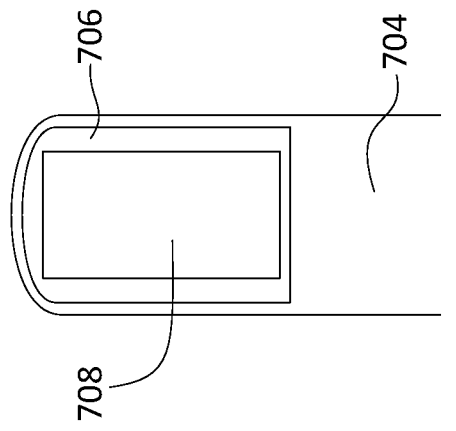
FIG. 7A and FIG. 7B illustrate an example of the compact 2D or 3D snapshot hyperspectral imaging probe device.
Figure 7A:
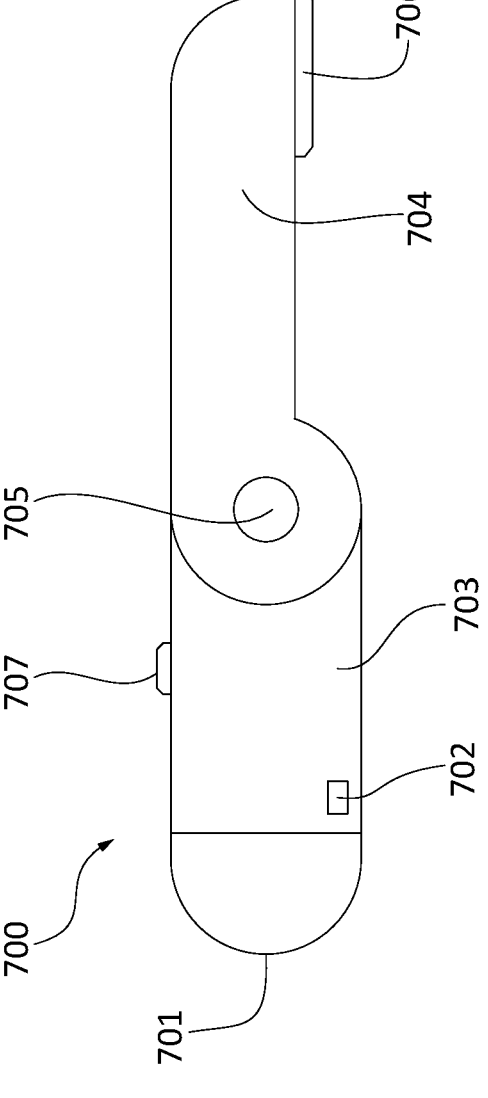

FIG. 7A and FIG. 7B shows an example of the compact 3D snapshot hyperspectral imaging probe device. The probe may have an integrated structured illumination apparatus and/or hyperspectral camera. The module 700 may be intended for handheld implementation. A microcontroller unit (MCU) and/or microprocessor unit (MPU) (not shown) may be housed in the base 701 of the device 700 and may be programmed through and input port 702 on the handle 703 of the module 700. The probe head 704 may contain the optics, electro-optics, opto-mechanics, and/or mechanical components (not shown) of the device. The probe head 704 may be rotated from 0 to 90 degrees about an axis point 705 near the center of the module 700. The illumination and collection port 706 may be located at the end of the probe.

Figure 8:
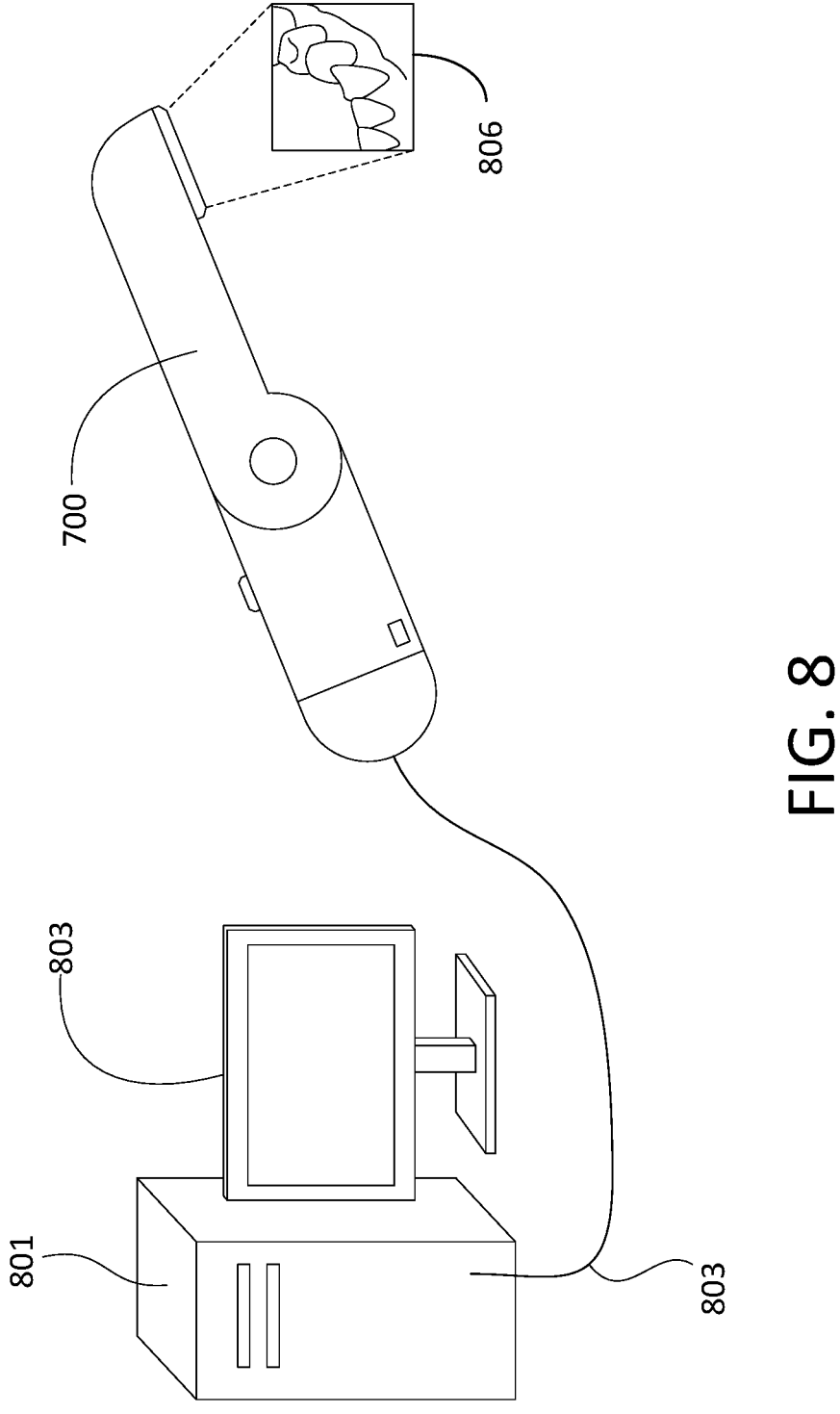
FIG. 8 illustrates an example of the compact 2D, or 3D snapshot hyperspectral imaging probe device of FIG. 7A and FIG. 7B with additional analysis components.

An image acquisition button 707 may be located on the handle 703. The illumination and collection port 706 may be protected with a window 708. The window 708 may be made of a material that may be transparent or near transparent to the illumination wavelengths. The module 700 may be connected to a computer 801 with display 802 via wire 803 or wireless connection, as shown in FIG. 8.

Power may be supplied to the probe using an external cord 803 or internal battery (not shown). The MCU and/or MPU may stream data to the computer 801. The data may be pre-analyzed by the onboard MCU and/or MPU. In some examples, the data may first be transferred to the computer 801 and then analyzed. The optical properties of the tissue sample 806 may be analyzed at each spectral wavelength available from the camera (not shown) and/or mapped to their 3D spatial location using mathematical triangulation/computational overlap. One or more algorithms may auto-stitch together snapshot images to create a larger field of view. The probe may be well suited for in vivo clinical diagnostics or investigations, and may be used for oral cavity applications, among other applications, for example.

One or more devices/systems may comprise employ one or more techniques for tissue scoring and product recommendation, as summarized in FIG. 3B. In one or more techniques, a machine learning algorithm(s) may be used to assign scores to the mapped tissue properties. For example, the tissue property scores may include properties such as body oil concentration, blood oxygenation, tissue oxygenation, tissue hydration, peeling, collagen density, lipid concentration, acne, burn severity, sun damage, wrinkles, rosacea, bacterial concentration, carcinogenesis, collagen structure, sub-surface angiography, rash severity, and/or skin pigmentation. In some examples, such as the face and full body scans, computer vision and machine learning may be used to detect specific sections of the face or body, such as eyes, periorbital region, cheeks, nose, lips, forehead, ears, chin, and other regions. In an example, the machine learning algorithm may classify the regions into different zones. Each zone may be scored according to the tissue properties acquired from the diagnostic device. In the method, an automated algorithm may access a product database stored either on the computer or the cloud.

In one or more scenarios, the accessed database may contain numerous products for tissue treatment. The optical properties derived from the diagnosis, the scoring, and the zones may be used to make automated specific product recommendations and/or improve user information. Selected product information, such as name, ingredients, usage area, usage frequency, dosage, purpose, price, and/or expected results may be displayed (e.g., immediately displayed) on a computer screen and/or sent to the users' wireless device and/or e-mail. The database may be updated (e.g., constantly updated) with new products and/or statistical information about efficacy for the benefit of the users. For example, the method may allow for user feedback to improve product selection. User feedback may be from the user giving specific allergies to products or ingredients, skin sensitivity, and/or previous experience with different other products. Device users/patients may input such information into a computer program or mobile device application. The machine learning algorithm(s) may incorporate the feedback when making product recommendations, for example.

Referring to FIG. 3A, a diagram 300 illustrates an example technique for indicating at least one property of a tissue sample. The technique/method/process may be performed by an imaging device, among other devices. The imaging device may comprise a memory, a light emitting projector, a camera, and/or a processor. At 302, the process may start or restart.

At 304, the imaging device may project at least some light on the tissue sample. At 306, the imaging device may control a capture of hyperspectral fluorescence image data of the tissue sample. The hyperspectral fluorescence image data may correspond at least to a first location in the tissue sample.

At 308, the imaging device may control a capture of spatial frequency domain imaging (SFDI) image data of the tissue sample. The SFDI image data may correspond at least to the first location in the tissue sample. At 310, the imaging device may process a first computational overlap of the hyperspectral fluorescence image data and the SFDI image data. The first computational overlap may comprise at least the first location in the tissue sample.

At 312, the imaging device may determine one or more properties of at least the first location of the tissue sample based, at least in part, on the first computational overlap of the hyperspectral fluorescence image data and the SFDI image data. At 314, the imaging device may generate a two-dimensional (2D), or a three-dimension (3D), spatial visual representation that may comprise at least the first location of the tissue sample based, at least in part, on the first computational overlap of the hyperspectral fluorescence image data and the SFDI image data. At 316, the process may stop or restart.

Referring to FIG. 3B, a diagram 350 illustrates an example technique for indicating products and/or product recommendations for one or more different zones of the tissue sample, perhaps based on a score applied to the one or more zones. The technique/method/process may be performed by an imaging device, among other devices. The imaging device may comprise a memory, a light emitting projector, a camera, and/or a processor. The imaging device may be in communication with a local communication network and/or the Internet. At 352, the process may start or restart.

At 354, the imaging device may acquire spectral and/or imaging data using a hyperspectral camera. At 356, the imaging device may process the data and/or may calculate one or more sample tissue properties. At 358, the imaging device may segment the sample tissue into one or more zones. The one or more zones may relate to specific products.

At 360, the imaging device may assign at least one score to one or more, or each zone. At 362, the imaging device may access online product database for one or more, or each zone. At 364, the imaging device may generate one or more lists of one or more recommended products/product information, based for example on the zone and/or the score.

At 366, the imaging device may send one or more recommendations and/or one or more product information to a mobile electronic device of a subject corresponding to the tissue sample, and/or to a display device, perhaps for example associated with the imaging device. At 368, the process may stop and/or restart.

Figure 4:
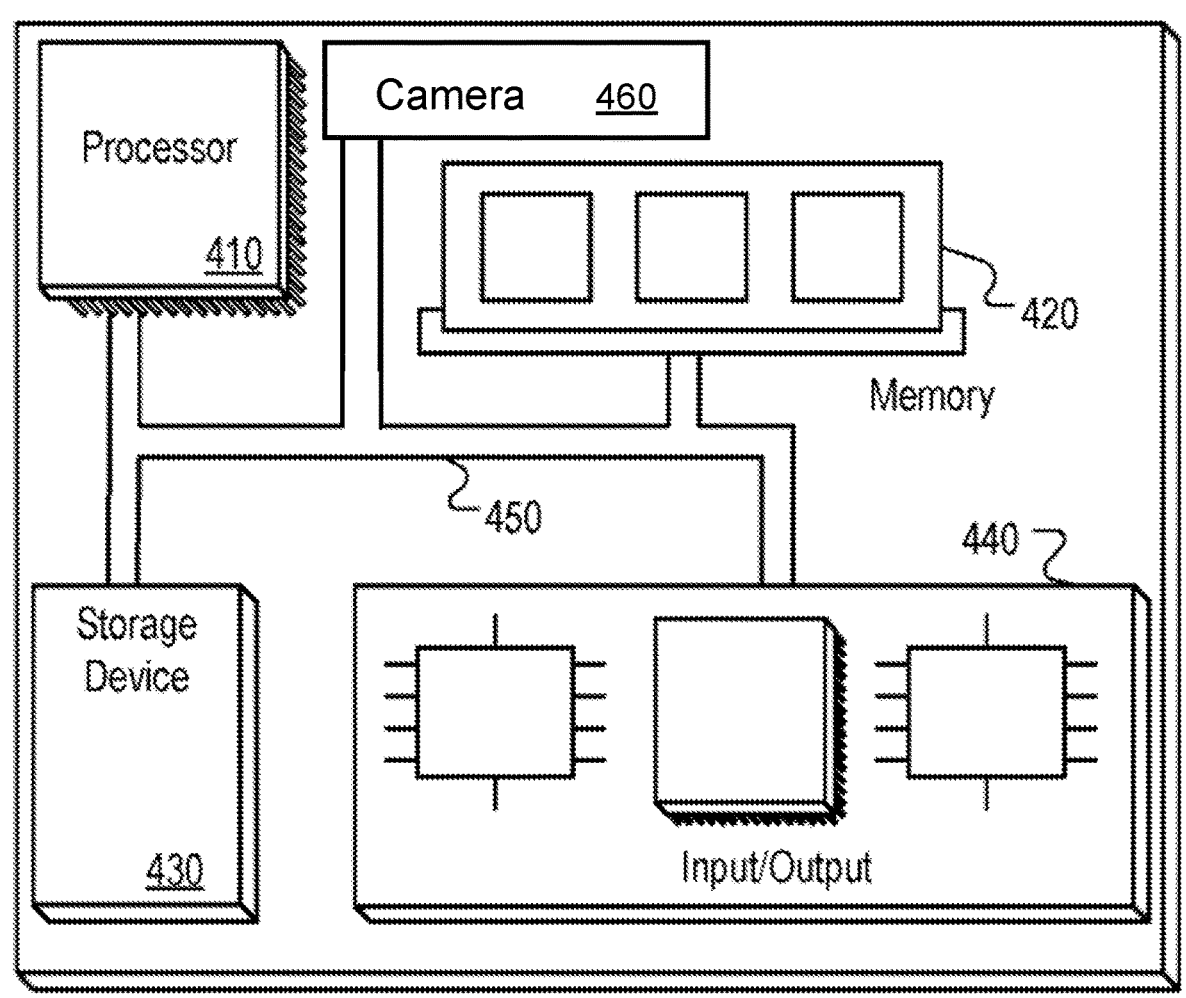
FIG. 4 is a block diagram of a hardware configuration of an example device that may control one or more parts of an imaging/scanning device and/or a technique performed by an imaging/scanning device.

FIG. 4 is a block diagram of a hardware configuration of an example device that may function as a process control device/logic controller of one or more of the imaging devices described herein, for example. The hardware configuration 400 may be operable to facilitate delivery of information from an internal server of a device. The hardware configuration 400 can include a processor 410, a memory 420, a storage device 430, and/or an input/output device 440. One or more of the components 410, 420, 430, and 440 can, for example, be interconnected using a system bus 450. The processor 410 can process instructions for execution within the hardware configuration 400. The processor 410 can be a single-threaded processor or the processor 410 can be a multi-threaded processor. The processor

410 can be capable of processing instructions stored in the memory 420 and/or on the storage device 430.

The memory 420 can store information within the hardware configuration 400. The memory 420 can be a computer-readable medium (CRM), for example, a non-transitory CRM. The memory 420 can be a volatile memory unit, and/or can be a non-volatile memory unit.

The storage device 430 can be capable of providing mass storage for the hardware configuration 400. The storage device 430 can be a computer-readable medium (CRM), for example, a non-transitory CRM. The storage device 430 can, for example, include a hard disk device, an optical disk device, flash memory and/or some other large capacity storage device. The storage device 430 can be a device external to the hardware configuration 400.

The input/output device 440 may provide input/output operations for the hardware configuration 400. The input/output device 440 (e.g., a transceiver device) can include one or more of a network interface device (e.g., an Ethernet card), a serial communication device (e.g., an RS-232 port), one or more universal serial bus (USB) interfaces (e.g., a USB 2.0 port) and/or a wireless interface device (e.g., an 802.11 card). The input/output device can include driver devices configured to send communications to, and/or receive communications from one or more networks (e.g., local network, the Internet, etc.). The input/output device 400 may be in communication with one or more input/output modules (not shown) that may be proximate to the hardware configuration 400 and/or may be remote from the hardware configuration 400. The one or more output modules may provide input/output functionality in the digital signal form, discrete signal form, TTL form, analog signal form, serial communication protocol, fieldbus protocol communication and/or other open or proprietary communication protocol, and/or the like.

The camera device 460 may provide digital video input/output capability for the hardware configuration 400. The camera device 460 may communicate with any of the elements of the hardware configuration 400, perhaps for example via system bus 450. The camera device 460 may capture digital images and/or may scan images of various kinds, such as Universal Product Code (UPC) codes and/or Quick Response (QR) codes, for example, among other images as described herein. In one or more scenarios, the camera device 460 may be the same and/or substantially similar to any of the other camera devices described herein.

The camera device 460 may include at least one microphone device and/or at least one speaker device. The input/output of the camera device 460 may include audio signals/packets/components, perhaps for example separate/separable from, or in some (e.g., separable) combination with, the video signals/packets/components the camera device 460. The camera device 460 may function as an imaging camera for one or more of the imaging devices described herein (e.g., a hyperspectral camera, among other kinds of imaging cameras).

The camera device 460 may also detect the presence of one or more people that may be proximate to the camera device 460 and/or may be in the same general space (e.g., the same room) as the camera device 460. The camera device 460 may gauge a general activity level (e.g., high activity, medium activity, and/or low activity) of one or more people that may be detected by the camera device 460. The camera device 460 may detect one or more general characteristics (e.g., height, body shape, skin color, pulse, heart rate, breathing count, etc.) of the one or more people detected by the camera device 460. The camera device 460 may be configured to recognize one or more specific people, for example.

The camera device 460 may be in wired and/or wireless communication with the hardware configuration 400. In one or more scenarios, the camera device 460 may be external to the hardware configuration 400. In one or more scenarios, the camera device 460 may be internal to the hardware configuration 400.

In one or more scenarios, any of the devices and/or techniques described herein may be implemented in 2D diagnostics and/or 3D diagnostics.

A multimodal, hyperspectral imaging system is described herein for timely diagnostics of tissues (e.g., skin tissue, oral tissue, etc.). The system/device termed for example Hyperspectral-Fluorescence-Spatial Frequency Domain Imaging (Hy-F-SFDI), may combine one or more principles/techniques of spatial frequency domain imaging, quantitative light fluorescence, and/or CIELAB color measurements. Hy-F-SFDI may be demonstrated by quantifying gingiva tissue hemoglobin volume fraction, hard tissue caries, bacterial activity, and/or whiteness. Hy-F-SFDI may employ a compact LED projector, excitation LED, and a 16 channel hyperspectral camera mounted on a custom platform for tissue imaging. A two-layer Monte Carlo approach may be used to generate a lookup table for quick tissue analysis. For clinical applications explanations/examples, among other applications, the system/device may be used for in vivo diagnosis of the oral hygiene of a subject/volunteer at different time points.

Development of spectroscopic imaging systems capable of timely, quantitative in vivo mapping of bio-chromophore concentrations may positively impact health diagnostics and/or drug development. Changes in bio-chromophores, such as blood, are indicators of disease and/or morbidity. Consequently, temporal mapping of chromophores may be clinically used to monitor and/or diagnose disease and/or pathology, as well as measure drug efficacy. Development of clinically applicable spectroscopic imaging systems/devices may be beneficial for tissue health diagnostics and/or drug development. At least one technical challenge for such devices/systems in applying spectroscopic imaging in clinical applications is the long image acquisition time and/or limited field-of-view (FOV).

One or more techniques for (e.g., large) FOV spectroscopic imaging may be snap-shot hyperspectral imaging. Fast image acquisition may improve spectroscopic analysis by minimizing motion artifacts. Motion artifacts may cause spatial mismatch in subsequent images that may be used in chromophore mapping. Snap-shot hyperspectral imaging may utilize broadband illumination, placing the burden of spectroscopy on the camera, whereas conventional spectral imaging may require time consuming multiplexing of light sources or tuning filters.

Spectral imaging may give two-dimensional convolved measurements of optical absorption and scattering from volumetric tissues. At least one approach for quantitative determination of tissue optical properties may be to decouple the absorption and scattering components of chromophores and tissues.

Spatial frequency domain imaging (SFDI) may be a reflection-based imaging technique that may separate the absorption and scattering components of a sample. SFDI may be used for quantitative determination of absorption and/or scattering properties. For example, SFDI may rely on measuring the percentage of light absorbed and/or the change in modulation depth of projected fringe patterns at different phases and frequencies, though alterations exist. An illumination field is described by $$I_{field}(r) = \frac{1}{2}[1 + \cos(\omega_r \cdot r)],$$

where r is the central position of the illumination field on the illumination plane and or is the spatial frequency of the illumination field in radians per unit length. When combined with tissue models, SFDI may be highly accurate for in vivo quantitative measurements of tissue chromophores (melanin and hemoglobin). However, SFDI is limited to chromophores with high optical absorption in the detectors spectral range (such as melanin and hemoglobin for visible light).

Comparatively, quantitative light fluorescence (QLF) may be a fluorescence-based imaging technique which may give access to chromophores that are difficult to detect using reflection-based techniques. QLF may be clinically used to qualitatively assess oral tissue health indicators such as specific tissue lesion area, porphyrin produced by bacterial activity, and changes in hard tissue mineralization. Combining hyperspectral imaging and QLF may allow for identification of fluorescent chromophore spectral signatures. In the case of hard tissue fluorescence, the shape of the fluorescence spectra may be used to classify tissue health. In one or more scenarios, spectral classification of hard tissue health in the oral cavity may be performed using spectral probes and/or qualitatively detected using fluorescence intensity with RGB cameras.

The quantitative chromophore mapping technique, Hyperspectral-Fluorescence-SFDI (Hy-F-SFDI), may increase the number of measurable chromophores by harnessing optical absorption, scattering, and/or fluorescence spectral mapping. The system/device may take advantage of snap-shot hyperspectral imaging for timely (0.6 Hz) multimodal SFDI and fluorescence imaging to investigate tissue health and hygiene in the oral cavity. SFDI results may be combined with a Monte Carlo approach for in vivo quantitative determination of melanin concentration and hemoglobin volume fraction. Spectral reflection and absorption may be utilized for CIELAB measurements of hard tissue. Fluorescence information may be used to detect bacteria activity (porphyrin) and hard tissue health. As described herein, systems/devices may provide a multimodal snap-shot hyperspectral imaging system which combines SFDI and fluorescence into a single platform for mapping oral hard and/or soft tissue parameters.

FIG. 9 shows a schematic of an example Hy-F-SFDI system/device 902. For SFDI and bright-field illumination, a compact LED projector (e.g., P2-A, AAXA Technologies) may be used. Light from the LED projector may be directed through a polarizer before being incident on the sample. Patterned light on the sample may be projected at spatial frequencies of 0 and 0.2 mm$^{-1}$ for the low and high frequency components, respectively. Each projected pattern may be incident on the sample for 100 ms. One or more images may be acquired for an 80 ms integration time, which may start 10 ms after each projected pattern.

Figure 10:
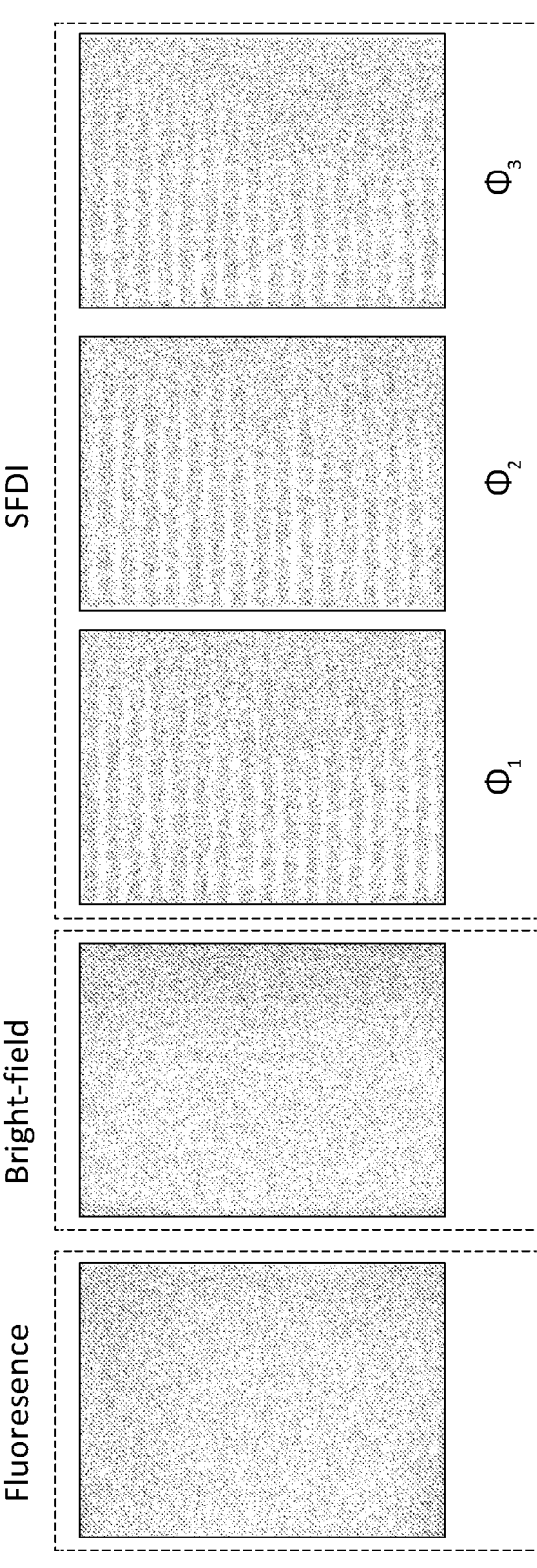
FIG. 10 is an example intensity profiles and illumination patterns of the Hy-F-SFDI system scattered from a phantom sample.

FIG. 10 shows images acquired from an example silicone phantom sample for SFDI. A total of five images may be acquired for SFDI (2-bright field, 3-structured light) in addition to two background images (not shown). The two bright-field images may be averaged and used for comparison with demodulated AC images. For fluorescence imaging, a 1200 mW 405 nm LED (e.g., M405LP1, Thorlabs) may be used to excite the sample. The excitation light may be passed (e.g., first passed) through a diffuser for homogenization. The light may be shaped using a condenser lens before passing through a linear polarizer (e.g., 25.5 AUF, Schneider Kreuznach) and being incident on the sample. To or more (e.g., two) fluorescence images may be acquired at 80 ms integration times.

Backscattered and/or fluorescent light from the sample may be passed through a cross-polarizer before being collected by a lens (e.g., C1614-M, Pentax) and detected with a 16-channel hyperspectral camera (e.g., MQ022HG-IM-SM4X4-VIS, Ximea). The nine-image acquisition time, including electronic latency, may be approximately 1.7 seconds. The measured central peak of the hyperspectral camera channels may range from 464-636 nm (central peak: 464, 468, 477, 487, 502, 512, 524, 538, 562, 573, 586, 598, 611, 620, 632, 636) and may have spectral bandwidths ranging from 12-22 nm for the full-width at half-max.

One or more algorithms may (e.g., written in LabVIEW, LabVIEW 2019, National Instruments) be used to synchronize optical irradiation and camera acquisition. A DAQ device (e.g., USB-6211, National Instruments) may be used for triggering camera acquisition and excitation LED illumination, while projector control may be handled using serial commands from the host computer. One or more images (e.g., nine images) may be collected for analysis (2-bright-field image, 3-structured light, 2-fluorescence, 2-background). Each image may be collected using an integration time of 80 ms. Illumination intensity and/or integration time may be chosen to avoid camera saturation, while allowing for sufficient signal. Image acquisition may start and end 10 ms after and before the illumination to allow for light source stabilization. Total sample image acquisition time, including background images, may be approximately 1.7 seconds due to software latency and hardware response.

One or more scenarios, hyperspectral image calibration and/or preprocessing may be conducted. Image calibration and processing may be performed using routines written in Matlab. FIG. 11 shows an example flow 1102 of at least three analysis/measurement techniques. A hyperspectral camera may be calibrated to analyze hyperspectral images. A camera manufacturer supplied correction matrix to raw images (e.g., FIG. 12A) using a Matlab program. The spectral response of each channel may be measured using a supercontinuum laser (e.g., SuperK Extreme, NKT) connected to an acousto-optic modulator (AOM). The laser may be routed through the Hy-F-SFDI system and reflected from a reflection standard (e.g., SG3151, SphereOptics). Using the AOM the wavelength may be controlled in 1 nm steps across the spectral range of the camera. One or more images may be acquired at one or more, or each, wavelength level.

Average output power and illumination area of the laser may be kept constant over the wavelengths in order to measure the system response. Background images may be averaged and subtracted from sample images (e.g., all sample images) to remove system noise. Each hyperspectral snapshot image (2048×1088 pixels) may be converted into a 512×272×16 hypercube (e.g., FIG. 12B). Adjustments may be made to the company provided correction matrix to account for significant spectral crosstalk in select channels. For hemoglobin and melanin fitting, the blue channels (464 nm, 468 nm, 477 nm, 487 nm) may be discarded due to spectral crosstalk that might not be sufficiently corrected in post processing.

FIG. 11 illustrates a processing flow of the Hy-F-SFDI system/device. Raw data may be first acquired. In the processing, a correction matrix may be applied and/or data may be converted into a hypercube. SFDI scattering and/or absorption, CIELAB, and/or fluorescence maps may be created. One or more parameter calculation algorithms may be applied for generating results.

The spectral calibration may be checked by measuring the absorption spectra of a MacBeth color checker (e.g., ColorChecker Classic, X-Rite) using the hyperspectral camera and compared the spectra with that acquired from a sub-nanometer resolution spectrometer (e.g., USB2000+VIS-NIR-ES, Ocean Optics).

Perhaps for example, to correct for non-uniform illumination from the light sources and system setup, among other reasons, the intensity profiles of the projector and/or excitation LED may be measured at the sample plane. For the projector illumination, the projected light may be reflected from the reflection standard. For the excitation LED, the fluorescence may be illuminated and/or measured from a homogenous silicone sample. Using a reflectance calibration standard, the projector light distribution profiles may be normalized over the field-of-view (FOV) and corrected for instrument response:

$$R = 0.95 * \frac{I - I_{dark}}{I_{white} - I_{dark}},$$

where I is the image, $I_{dark}$ is the background image, and $I_{white}$ is the white reflectance standard image. The fluorescence intensity profile may be post corrected by dividing the raw image by a normalized intensity field. The curvature of the sample surface may not be considered in the final results and can induce error if significant curvature exists. In one or more scenarios, perhaps (e.g., only) relatively flat areas in the imaging plane may be used for analysis.

FIG. 12A illustrates an example of the raw hyperspectral fluorescence (top) and bright-field (bottom) images acquired from a subject/volunteer. A zoomed image from the raw data, indicated by the dotted square in the image, is displayed to show the 4×4 filter matrix over the pixels. Porphyrin emission can visually be distinguished from the raw fluorescence image around the hard and soft tissue (e.g., might not be obvious in the bright-field). FIG. 12B illustrates an example of a reconstructed hypercube displaying the spectral imaging ability of the detector.

For SFDI analysis, single frequency, three-phase SFDI may be used for measuring absorption and reduced scattering coefficients of the samples. An open source SFDI Matlab code (Open SFDI) may be modified for use with the hyperspectral camera and the custom Monte Carlo (MC) lookup table (LUT). The principles of SFDI have been described herein. To extract subsurface optical properties the AC components ($M_{AC}$) of the high frequency data were recovered using the demodulation equation:

$$M_{AC}(x, y) = \frac{\sqrt{2}}{3} * \sqrt{[I_{1,A}(x, y) - I_{2,A}(x, y)]^2 + [I_{2,A}(x, y) - I_{3,A}(x, y)]^2 + [I_{3,A}(x, y) - I_{1,A}(x, y)]^2}$$

where $I_{1,A}$, $I_{2,A}$, and $I_{3,A}$ are the high frequency structured images. The DC components of the images may be calculated as:

$$M_{DC}(x, y) = \frac{1}{3} * [I_{1,A}(x, y) + I_{2,A}(x, y) + I_{3,A}(x, y)].$$

where $M_{AC,ref}$ is the modulated AC components measured from a reflection standard and $R_{d,ref}$ is the measured diffuse reflectance of the same standard.

An inverse forward MC simulation may be used to create a LUT to determine chromophore concentration from the SFDI absorption ($\mu_a$) and reduced scattering coefficients ($\mu'_s$). The MC simulation may use a two-layer model. The MC model may use the absolute diffuse reflectance values to solve for unique $\mu_a$ and $\mu'_s$ values. The MC model may have five variables to fit the measured data. The first layer may be considered to contain all melanin without blood, whereas the second layer may be considered to contain blood without melanin. The melanin fraction ($C_{mel}$), blood fraction ($C_{blood}$), blood oxygen saturation ($S_b$), and/or oral mucosa epithelium thickness (T) may be varied in the simulation to create expected $\mu_a$ and $\mu'_s$. The simulated values may be placed in a MC LUT for each spectral channel of the hyperspectral camera for $\mu_a$ and $\mu'_s$. The simulation may use the best spectral fit from the LUT to approximate the melanin fraction, blood fraction and oxygen saturation at each pixel in the hyperspectral images using the known absorption and scattering coefficients of the chromophore and tissues:

$$\mu_a(\lambda) = M*\mu_{mel}(\lambda) + B*SO_2*\mu_{oxy}(\lambda) + B*(1-SO_2)*\mu_{oxy}(\lambda)$$

where scattering is described by the Henyey-Greenstein phase function for both layers:

$$\mu'_s = \alpha*\left(\frac{\lambda}{500}\right)^{-\beta}.$$

Here a is the wavelength scaling factor and $\beta$ is the scattering power as is understood in the art. In one or more scenarios, the blue channels might not be used (464 nm, 468 nm, 477 nm, 487 nm) in the MC analysis, perhaps for example due to significant crosstalk from red light, among other reasons.

The hyperspectral camera may be calibrated for CIE-LAB 1976 measurements using the bright-field image. Each 4×4 hyperspectral pixel may be converted into XYZ values of the CIE-LAB 1976 color system. The XYZ values may be transformed into LAB values. Processing may be performed using routines written in Matlab. The calibration may be verified by measuring the CIE-LAB values of a MacBeth color checker. The values may be calibrated using squares 1-10 of the Macbeth ColorChecker. Squares 11-18 may be used to confirm calibration and avoid over fitting. For homogenous measurements, 100 pixels may be averaged in a 10×10 square on the selected part of the MacBeth color checker. L may be calibrated using the neutral colors (squares 19-24) and scaled to the camera dynamic range.

For fluorescence analysis, fluorescence spectra may be acquired, as described herein. The spectral correction matrix may be applied to fluorescence images for calibration. The acquired spectra may be used to distinguish carries, porphyrin, dentine and enamel, which may have spectra (e.g., well documented spectra). Fluorescence may detect implants in the oral cavity. Blue channels may be incorporated in fluorescence analysis, as the low red fluorescence from porphyrin and caries may be post corrected.

Homogenous phantoms may be used to validate the ability of the Hy-F-SFDI system to measure $\mu_a$ and $\mu'_s$. $\mu_a$ and $\mu'_s$ of silicone phantoms may be measured using the inverse adding-doubling method (IAD). In one or more scenarios, a single integrating sphere (e.g., 819C-SL-5.3-CAL2, Newport) may be used for transmission and absorption measurements of the samples and reference target. A supercontinuum laser may be used, in combination with the AOM, to illuminate the samples at the central wavelengths of the spectral channels used in the MC simulations. To measure absorbed and transmitted light, a spectrometer may be coupled to the detector port of the integrating sphere with a multimode fiber (79-100272-00, C Technologies Inc.). The sample may be uniformly cut to 1 mm thickness and the collimated laser beam diameter may be 2 mm.

In vivo Hy-F-SFDI measurements of oral tissues may be acquired, for example, from a volunteer. Two measurements may be taken at different time points and different oral hygiene conditions. The baseline measurement may be acquired from the volunteer during their normal hygiene regiment. The second measurement may be acquired from the same volunteer after three weeks of non-brushing in order to induce mild tissue inflammation. The subject/volunteer may be given an oral exam by a dental professional at both time points to measure the gingival index (GI) of gums surrounding the front teeth. To keep the subjects/volunteer's oral cavity fixed at the correct distance in the imaging plane, a chin rest with head harness may be used. To expose the gingiva and hard tissue, the subject/volunteer may wear a cheek retractor during the imaging sessions. The subject/volunteer may wear safety goggles to prevent eye exposure to the excitation LED. The subject/volunteer may remain still during image acquisition to reduce motion artifacts. Image acquisition may last 1.7 seconds, including 200 ms for background images acquired after the SFDI and fluorescence images. Hy-F-SFDI tissue analysis may be limited to relatively flat regions of the imaging plane that may easily be illuminated to reduce distance variation induced errors.

Table 1 shows example results of the IAD and Hy-F-SFDI measurements of the skin mimicking phantom for the relevant spectral channels. IAD and Hy-F-SFDI $\mu_a$ and $\mu'_s$ measurements may be similar across the spectrum. Reduced scattering coefficient measurements may generally be within 5% error, with the exception of the 636 nm channel. Absorption coefficient measurements may be in relative agreement across the two techniques. The 586 nm channel and lower values of $\mu_a$ may have (e.g., significant) error. The error may likely be due to using a narrow band laser for the IAD experiments and a broad LED for Hy-F-SFDI. The larger bandwidth of the channels may result in a significantly different $\mu_a$ and $\mu'_s$ value. In one or more scenarios, some spectral crosstalk may be present in the post-corrected Hy-F-SFDI, which may induce error in the final measurement. Though IAD is known to have experimental error, may be used as the standard in investigations.

TABLE 1

| Average Hy-F-SFDI vs IAD measured optical coefficients | | | | | | | | | | | |
| --- | --- | --- | --- | --- | --- | --- | --- | --- | --- | --- | --- |
| Wavelength (nm) | | | | | | | | | | | |
| 502 | 512 | 524 | 538 | 562 | 573 | 586 | 598 | 611 | 620 | 632 | 636 |
| Hy-F-SFDI ($cm^{-1}$) | | | | | | | | | | | |
| $\mu_a$ | | | | | | | | | | | |
| 3.856 | 3.752 | 2.610 | 2.250 | 1.500 | 1.020 | 0.290 | 0.013 | 0.013 | 0.011 | 0.002 | 0.001 |
| $\mu'_s$ 40.92 | 35.50 | 35.97 | 36.04 | 36.80 | 40.04 | 44.52 | 51.80 | 64.56 | 69.52 | 67.32 | 62.48 |
| IAD ($cm^{-1}$) | | | | | | | | | | | |
| $\mu_a$ 4.262 | 3.410 | 2.600 | 2.200 | 1.480 | 0.961 | 0.362 | 0.040 | 0.011 | 0.009 | 0.002 | 0.002 |
| $\mu'_s$ 42.29 | 35.49 | 36.38 | 35.89 | 36.21 | 38.57 | 46.21 | 52.21 | 66.28 | 68.52 | 67.13 | 67.58 |

FIG. 13A, FIG. 13B, and FIG. 13C shows a single channel analysis from the Hy-F-SFDI of a subjects/volunteers' oral cavity before and after abstaining from brushing for three weeks. $\mu_a$ and $\mu'$ of the oral cavity may be mapped. The $\mu_a$ and $\mu'$ for an area in the upper gingiva, indicated by a white dotted box in FIG. 13A and FIG. 13B, may be averaged and plotted over the spectral range for the base and three-week data in FIG. 13C. In the plots, a significant change in the absorption and less pronounced change in scattering may be distinguished at the two time points.

FIG. 13A illustrates mapped tissue absorption coefficient at the 502 nm spectral channel for the base (top map) and 3-week (bottom map) time points. FIG. 13B illustrates the same as in FIG. 13A, but for a reduced scattering coefficient. FIG. 13C illustrates a plot of the averaged absorption and reduced scattering coefficients for each spectral channel. The data were averaged from the region indicated in the white dotted box in FIG. 13A and FIG. 13B.

Sample motion might not be a significant factor for in vivo Hy-F-SFDI. The fast acquisition time and stable chin rest with head restraint may minimize movement from the volunteer during imaging. Though the system/device may require a total of nine images for complete diagnostics, only five images may be useful/necessary for the SFDI modality. Of the five useful/necessary images, at least two images may be background and may not be sensitive to motion of the target. The total time for the SFDI acquisition may be 0.9 seconds (1.1 Hz). This time may be improved by using the summed high frequency components for the DC image, increasing illumination intensity, decreasing detector integration time, and reducing latency of software and hardware.

The SFDI modality imaging rate may fundamentally be limited by the projector DMD array to 30 Hz per image (6 Hz for all five SFDI images). Addition of a faster DMD array and/or lowering bit resolution may double acquisition rate (>12 Hz for all SFDI). Higher frame rates may make possible real-time monitoring of hemoglobin. The hyperspectral snapshot camera may sacrifice resolution for spectral information. The lower resolution may contribute to reducing apparent motion artifacts in the reconstructed images, and/or may prevent structural evaluation of smaller vasculature. Higher pixel number cameras may overcome the resolution limitation, and/or might produce larger error from motion, for example.

Figures 14A, 14B, 14C, 14D:
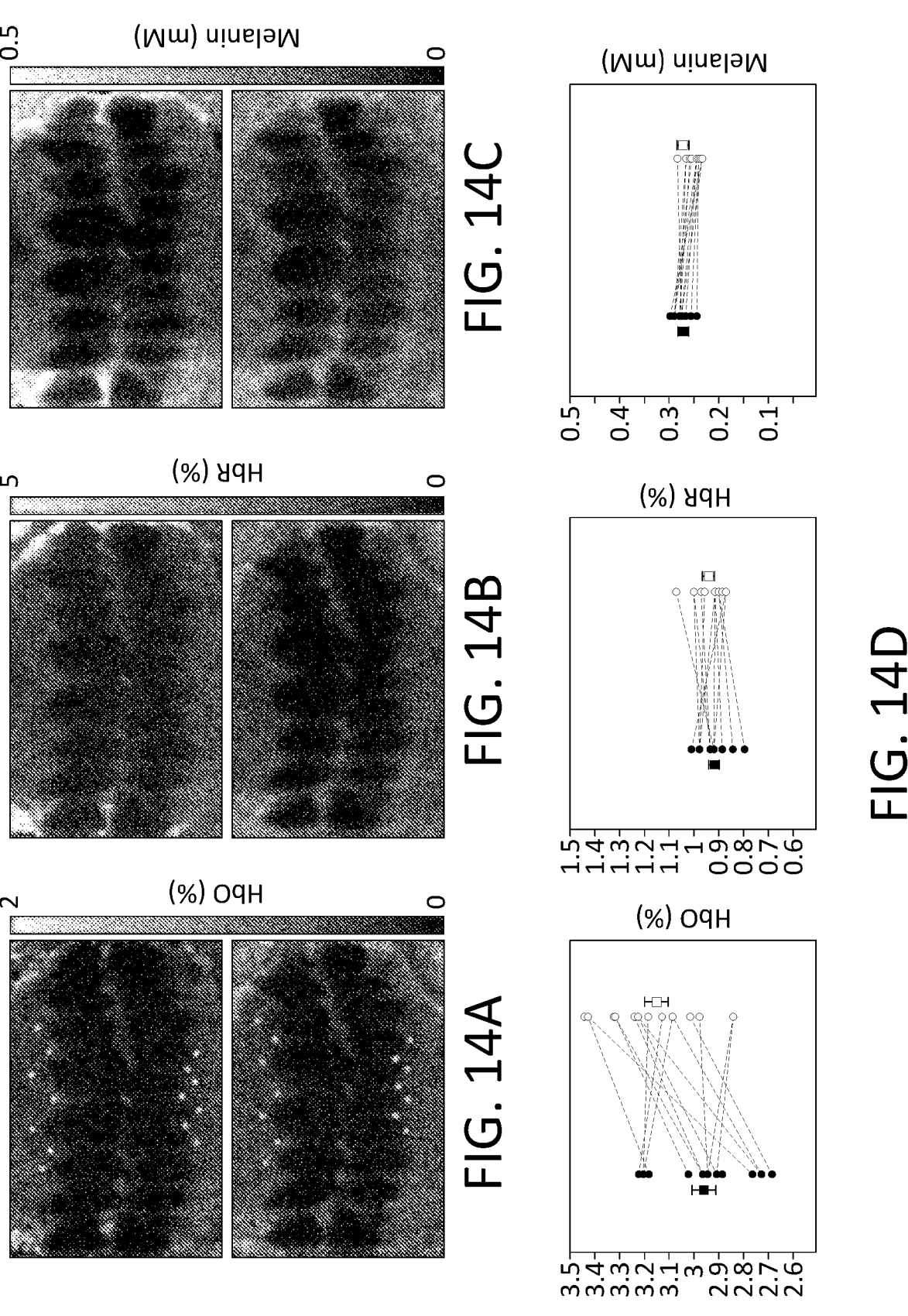
FIG. 14A, FIG. 14B, FIG. 14C, and FIG. 14D illustrate examples of the volume fraction change calculated in total Hb, HbR, HbO and melanin at different sections of the gingiva.

The volume fraction change may be calculated in total Hb, HbR, HbO and melanin at different sections of the gingiva, as shown in FIG. 14A, FIG. 14B, FIG. 14C, and FIG. 14C. MC fitting for the oxygenated blood, de-oxygenated blood, and melanin chromophores may be used at each hyperspectral pixel to determine chromophore concentration. Using the MC results, chromophore maps may be generated at each time point, as shown in FIG. 14A, FIG. 14B, and FIG. 14C. To understand how chromophore concentration in localized regions of the tissue may change, the average value may be determined at 14 locations in the oral cavity of the chromophores at both time points. A 4×4 pixel region may be averaged at the locations indicated by the dots in FIG. 14A.

FIG. 14A illustrates oxygenated blood map of the base (top) and three-week (bottom) time points. FIG. 14B illustrates the same as FIG. 14A, but for deoxygenated blood. FIG. 14C illustrates the same as FIG. 14A, but for melanin. FIG. 14D illustrates measurements of the oxygenated blood volume fraction (left), deoxygenated blood volume fraction (middle), and melanin molar concentration (right). The locations of the measurements are indicated by the white dots in FIG. 14A. Error bars indicate the standard error of the mean (SEM).

The locations in the two images (e.g., FIG. 14A) may be approximated by matching features in the corresponding white light images. Though large field-of-view blood volume maps of the oral cavity may not have been thoroughly investigated, the measured values (shown in FIG. 14C) may be within the expected biological range. Comparison may show a significant change in oxygenated blood volume fraction near the gingival margin ($\Delta$HbO=+0.210), whereas deoxygenated blood ($\Delta$HbR=+0.033) and melanin concentration ($\Delta$melanin=+0.0023 mM) may not significantly change. Quantitative results may be consistent with the average measured GI score of the front teeth (base=1.25, final=2.08), which qualitatively shows increased inflammation. Small changes in melanin may be expected due to tissue conformational changes from swelling and minor alignment changes in the system. Analysis may be limited to relatively flat regions of the tissue to limit curvature induced error.

Figure 15A:
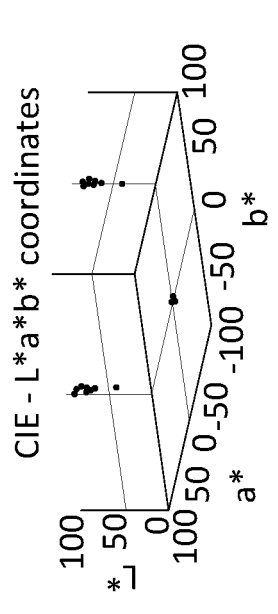
FIG. 15A, FIG. 15B, FIG. 15C, and FIG. 15D show example experimental CIE-LAB and fluorescence results from Hy-F-SFDI analysis of the subject/volunteer.
Figure 15B:
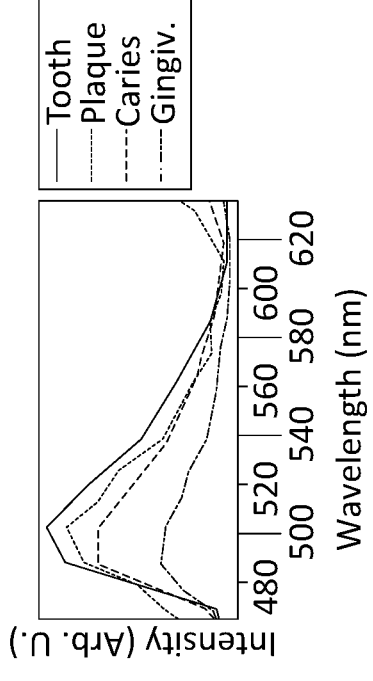

FIG. 15A, FIG. 15B, FIG. 15C, and FIG. 15D show example CIE-LAB and fluorescence results from Hy-F-SFDI analysis of the subject/volunteer. A color corrected white light image may be generated using the CIE-LAB calibration procedure as shown in FIG. 15A (as adjusted for black and white view). The CIE-LAB values of 17 well exposed teeth may be measured. Using the International Standards Organization Designation System (ISO System), numbers 11-14, 21-23, 31-35, and 41-45 may be assigned to the measured teeth. The CIE-LAB values may be collectively plotted as shown in FIG. 15B. The measurements may range from −0.3-2.1 and 1.9-14.4 for the 'a*' and 'b*' values, respectively. Intensity measurements, L, of each tooth may range from 42 to 91. Teeth implants in positions 14, 35 and 45 may have the highest L values compared to real teeth (real teeth may have an average L value of 74.3).

Figure 15C:
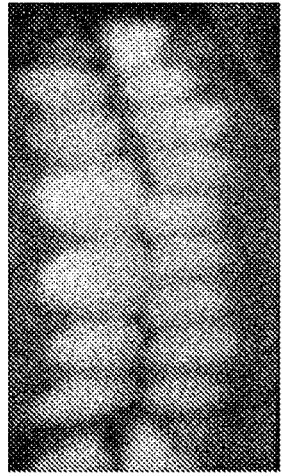
Figure 15D:
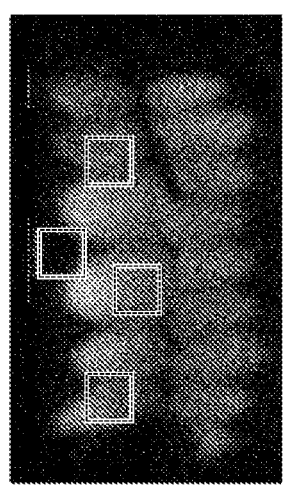

Fluorescence imaging shown in FIG. 15C may identify implants due to their lack of fluorescence. Hyperspectral fluorescence imaging may capture the spectral signatures of dentine, plaque and caries as shown in FIG. 15D. Depending on severity, spectra of surface carries (FIG. 15C, fourth white dotted box from right) may be characterized by a caries shifted peak with a slight plaque peak (e.g., centered at 630 nm, not shown) when compared with healthy dentine fluorescence (FIG. 15C, second white dotted box from right), whereas plaque (FIG. 15C, first white dotted box from right) may be distinguished by a porphyrin emission peak, not shown.

Caries severity measurements based on fluorescence might not be standardized in literature, but may often be performed using the intensity difference or ratio of the red and green channels. Caries severity may be classified into levels using the ICDAS II criteria (0-healthy, 6-severe decay). In a classification measurement, the red spectral channels (620, 632, and 636 nm channels) may be summed, where caries emission may be present, and several green spectral channels (487, 502, and 512 nm) indicative of healthy tissue, to create a red and green score. The red and the green score may be divided to get a ratio that may diagnosis the levels on the ICDAS II scale. One or more techniques may be utilized to match existing classification methods. Spectral mapping may allow for an extra dimension of caries evaluation that may be harnessed to measure caries severity.

FIG. 15A, FIG. 15B, FIG. 15C, and FIG. 15D illustrate white light and autofluorescence analysis of tissue hygiene. FIG. 15A illustrates reconstructed white light image of the oral cavity (adjusted for black and white view). FIG. 15B illustrates CIELAB measurements of 17 visible teeth. The molar implants have higher L values in the reconstructed image. FIG. 15C illustrates pseudo colored (adjusted for black and white view) fluorescence image displaying hard-tissue, caries, and porphyrin fluorescence. FIG. 15D illustrates measured spectra of different sections of the oral cavity. The spectra are averaged from the region indicated by the boxes in FIG. 15A.

As described herein, Hy-F-SFDI may benefit longitudinal clinical investigations of oral health and oral product efficacy investigations that require quantitative functional information and bacterial activity for mode-of-action analysis. The strength of Hy-F-SFDI may be the large field-of-view, timely imaging and ability to simultaneously detect more chromophores than visible SFDI alone has demonstrated. Hy-F-SFDI's ability for contact free, in vivo multimodal imaging is presented. Hy-F-SFDI may be used to generate quantitative longitudinal maps of chromophore tissue concentrations, bacterial activity, hard tissue, and CIE-LAB color values may be measured in the oral cavity. One or more configurations described herein may provide a (e.g., relatively simplified) non-invasive approach for in vivo oral tissue diagnostics. In one or more scenarios, accounting for surface curvature by implementing three-dimensional SFDI may improve system accuracy and/or applicability.

The subject matter of this disclosure, and components thereof, can be realized by instructions that upon execution cause one or more processing devices to carry out the processes and/or functions described herein. Such instructions can, for example, comprise interpreted instructions, such as script instructions, e.g., JavaScript or ECMAScript instructions, or executable code, and/or other instructions stored in a computer readable medium.

Implementations of the subject matter and/or the functional operations described in this specification and/or the accompanying figures can be provided in digital electronic circuitry, in computer software, firmware, and/or hardware, including the structures disclosed in this specification and their structural equivalents, and/or in combinations of one or more of them. The subject matter described in this specification can be implemented as one or more computer program products, e.g., one or more modules of computer program instructions encoded on a tangible program carrier for execution by, and/or to control the operation of, data processing apparatus.

A computer program (also known as a program, software, software application, script, or code) can be written in any form of programming language, including compiled or interpreted languages, and/or declarative or procedural languages. It can be deployed in any form, including as a stand-alone program or as a module, component, subroutine, and/or other unit suitable for use in a computing environment. A computer program may or might not correspond to a file in a file system. A program can be stored in a portion of a file that holds other programs and/or data (e.g., one or more scripts stored in a markup language document), in a single file dedicated to the program in question, and/or in multiple coordinated files (e.g., files that store one or more modules, sub programs, or portions of code). A computer program can be deployed to be executed on one computer or on multiple computers that may be located at one site or distributed across multiple sites and/or interconnected by a communication network.

The processes and/or logic flows described in this specification and/or in the accompanying figures may be performed by one or more programmable processors executing one or more computer programs to perform functions by operating on input data and/or generating output, thereby tying the process to a particular machine (e.g., a machine programmed to perform the processes described herein). The processes and/or logic flows can also be performed by, and apparatus can also be implemented as, special purpose logic circuitry, e.g., an FPGA (field programmable gate array) and/or an ASIC (application specific integrated circuit).

Computer readable media suitable for storing computer program instructions and/or data may include all forms of non-volatile memory, media and memory devices, including by way of example semiconductor memory devices (e.g., EPROM, EEPROM, and/or flash memory devices); magnetic disks (e.g., internal hard disks or removable disks); magneto optical disks; and/or CD ROM and DVD ROM disks. The processor and/or the memory can be supplemented by, or incorporated in, special purpose logic circuitry.

While this specification and the accompanying figures contain many specific implementation details, these should not be construed as limitations on the scope of any invention and/or of what may be claimed, but rather as descriptions of features that may be specific to described example implementations. Certain features that are described in this specification in the context of separate implementations can also be implemented in combination in perhaps one implementation. Various features that are described in the context of perhaps one implementation can also be implemented in multiple combinations separately or in any suitable sub-combination. Although features may be described above as acting in certain combinations and/or perhaps even (e.g., initially) claimed as such, one or more features from a claimed combination can in some cases be excised from the combination. The claimed combination may be directed to a sub-combination and/or variation of a sub-combination.

While operations may be depicted in the drawings in an order, this should not be understood as requiring that such operations be performed in the particular order shown and/or in sequential order, and/or that all illustrated operations be performed, to achieve useful outcomes. The described program components and/or systems can generally be integrated together in a single software product and/or packaged into multiple software products.

Examples of the subject matter described in this specification have been described. The actions recited in the claims can be performed in a different order and still achieve useful outcomes, unless expressly noted otherwise. For example, the processes depicted in the accompanying figures do not require the particular order shown, and/or sequential order, to achieve useful outcomes. Multitasking and parallel processing may be advantageous in one or more scenarios.

While the present disclosure has been illustrated and described in detail in the drawings and foregoing description, the same is to be considered as illustrative and not restrictive in character, it being understood that only certain examples have been shown and described, and that all changes and modifications that come within the spirit of the present disclosure are desired to be protected.

What is claimed is:

1. An imaging device configured to indicate at least one property of a tissue sample, the imaging device comprising:
   a memory;
   a light emitting projector;
   a camera; and
   a processor, the processor configured at least to:
      project light on the tissue sample;
      control a capture of hyperspectral fluorescence image data of the tissue sample, the hyperspectral fluorescence image data corresponding at least to a first location in the tissue sample;
      control a capture of spatial frequency domain imaging (SFDI) image data of the tissue sample, the SFDI image data corresponding at least to the first location in the tissue sample, wherein the hyperspectral fluorescence image data and the SFDI image data correspond to a substantial entirety of the tissue sample;
      process a first computational overlap of the hyperspectral fluorescence image data and the SFDI image data, the first computational overlap comprising at least the first location in the tissue sample;
      determine one or more properties of at least the first location of the tissue sample based, at least in part, on the first computational overlap of the hyperspectral fluorescence image data and the SFDI image data, wherein determining the one or more properties comprises fitting SFDI-derived optical absorption and reduced scattering maps, derived from the SFDI image data, to a two-layer Monte Carlo look-up table modeling a first layer containing melanin without blood and a second layer containing blood without melanin;
      segment the tissue sample into one or more zones based on the hyperspectral fluorescence image data and the SFDI image data; and
      generate at least one of: a two-dimensional (2D), or a three-dimension (3D), spatial visual representation comprising at least the first location of the tissue sample based, at least in part, on the first computational overlap of the hyperspectral fluorescence image data and the SFDI image data.

2. The device of claim 1, wherein the hyperspectral fluorescence image data further corresponds at least to a second location in the tissue sample, and the SFDI image data further corresponds at least to the second location in the tissue sample, the processor being further configured to:
   process a second computational overlap of the hyperspectral fluorescence image data and the SFDI image data, the second computational overlap further comprising at least the second location in the tissue sample; and
   determine one or more properties of at least the second location of the tissue sample based, at least in part, on the second computational overlap, the at least one of: the two-dimensional (2D), or the three-dimension (3D), spatial visual representation further comprising at least the second location of the tissue sample, the spatial visual representation being further based, at least in part, on the second computational overlap.

3. The device of claim 1, wherein the processor is further configured to:
   generate at least a first image of the tissue sample based on the hyperspectral fluorescence image data, the first image of the tissue sample depicting at least the first location in the tissue sample; and
   generate at least a second image of the tissue sample based on the SFDI image data, the second image of the tissue sample depicting at least the first location in the tissue sample.

4. The device of claim 1, wherein the processor is further configured such that at least one of: the two-dimensional (2D), or the three-dimension (3D), spatial visual representation further comprises an indication of at least the first location in the tissue sample.

5. The device of claim 1, wherein the processor is further configured to:
   identify at least one condition corresponding to at least the first location in the tissue sample based, at least in part, on the first computational overlap of the hyperspectral fluorescence image data and the SFDI image data.

6. The device of claim 5, wherein the processor is further configured such that at least one of: the two-dimensional (2D), or the three-dimension (3D), spatial visual representation further comprises an indication of the at least one condition corresponding to the first location in the tissue sample.

7. The device of claim 5, wherein the processor is further configured such that the at least one condition is one or more of: plaque, tooth decay, gingivitis, periodontitis, dehydrated skin, atopic dermatitis, eczema or a tissue condition.

8. The device of claim 5, wherein the tissue sample is at least one of: skin tissue, or an oral cavity tissue.

9. The device of claim 8, wherein the at least one condition corresponds to a dental disease of the oral cavity tissue.

10. The device of claim 1, wherein the one or more properties of at least the first location of the tissue sample is at least one of: the SFDI-derived optical absorption, optical scattering, body oil concentration, blood oxygenation, tissue oxygenation, tissue hydration, peeling, collagen density, lipid concentration, acne, burn severity, sun damage, wrinkles, rosacea, bacterial concentration, carcinogenesis, collagen structure, sub-surface angiography, rash severity, or skin pigmentation.

11. The device of claim 1, wherein the camera is a hyperspectral camera.

12. The device of claim 1, wherein the light projector comprises at least one of: a light emitting diode (LED)

projector, a broadband illumination source, a digital micro-mirror device (DMD) array, or a digital light processing (DLP) array.

13. The device of claim 1, wherein the processor is further configured to:

determine at least one of: one or more properties of each of the one or more zones, or one or more conditions of each of the one or more zones, based, at least in part, on the hyperspectral fluorescence image data and the SFDI image data; and assign a score to each of the one or more zones using machine learning, the assigned score being based on at least one of: the one or more properties of each of the one or more zones, or the one or more conditions of each of the one or more zones.

14. The device of claim 13, wherein the device is in communication with the Internet, and the processor is further configured to:

initiate an Internet-based search of one or more treatment products corresponding to at least some of the one or more zones based, at least in part, on the score of the at least some of the one or more zones.

15. The device of claim 1, wherein the processor is configured such that the capture of at least one of: the hyperspectral fluorescence image data of the tissue sample, or the SFDI image data of the tissue sample, is an in-vivo capture.

16. A method for indicating at least one property of a tissue sample performed by an imaging device, the imaging device comprising a memory, a light emitting projector, a camera, and a processor, the method comprising:

projecting, via the projector, light on the tissue sample;

controlling, via the processor, a capture of hyperspectral fluorescence image data of the tissue sample, the hyperspectral fluorescence image data corresponding at least to a first location in the tissue sample;

controlling, via the processor, a capture of spatial frequency domain imaging (SFDI) image data of the tissue sample, the SFDI image data corresponding at least to the first location in the tissue sample, wherein the hyperspectral fluorescence image data and the SFDI image data correspond to a substantial entirety of the tissue sample;

processing, via the processor, a first computational overlap of the hyperspectral fluorescence image data and the SFDI image data, the first computational overlap comprising at least the first location in the tissue sample;

determining, via the processor, one or more properties of at least the first location of the tissue sample based, at least in part, on the first computational overlap of the hyperspectral fluorescence image data and the SFDI image data, wherein determining the one or more properties comprises fitting SFDI-derived optical absorption and reduced scattering maps, derived from the SFDI image data, to a two-layer Monte Carlo look-up table modeling a first layer containing melanin without blood and a second layer containing blood without melanin;

segmenting, via the processor, the tissue sample into one or more zones based on the hyperspectral fluorescence image data and the SFDI image data; and generating, via the processor, at least one of: a two-dimensional (2D), or a three-dimension (3D), spatial visual representation comprising at least the first location of the tissue sample based, at least in part, on the first computational overlap of the hyperspectral fluorescence image data and the SFDI image data.

17. The method of claim 16, wherein the hyperspectral fluorescence image data further corresponds at least to a second location in the tissue sample, and the SFDI image data further corresponds at least to the second location in the tissue sample, the method further comprising:

processing, via the processor, a second computational overlap of the hyperspectral fluorescence image data and the SFDI image data, the second computational overlap further comprising at least the second location in the tissue sample; and determining, via the processor, one or more properties of at least the second location of the tissue sample based, at least in part, on the second computational overlap, the at least one of: the two-dimensional (2D), or the three-dimension (3D), spatial visual representation further comprising at least the second location of the tissue sample, the spatial visual representation being further based, at least in part, on the second computational overlap.

18. The method of claim 16, further comprising:

generating, via the processor, at least a first image of the tissue sample based on the hyperspectral fluorescence image data, the first image of the tissue sample depicting at least the first location in the tissue sample; and generating, via the processor, at least a second image of the tissue sample based on the SFDI image data, the second image of the tissue sample depicting at least the first location in the tissue sample.

19. The method of claim 16, further comprising:

generating, via the processor, an indication of at least the first location in the tissue sample on at least one of: the two-dimensional (2D), or the three-dimension (3D), spatial visual representation.

20. The method of claim 16, further comprising:

identifying, via the processor, at least one condition corresponding to at least the first location in the tissue sample based, at least in part, on the first computational overlap of the hyperspectral fluorescence image data and the SFDI image data.

* * * * *